United States Patent
Simons et al.

[11] Patent Number: 5,971,941
[45] Date of Patent: Oct. 26, 1999

[54] INTEGRATED SYSTEM AND METHOD FOR SAMPLING BLOOD AND ANALYSIS

[75] Inventors: Tad Decatur Simons, Palo Alto; Michael Greenstein, Los Altos; Dominique Freeman, Pascadero; Leslie Anne Leonard, Portola; David A. King, Menlo Park; Paul Lum, Los Altos, all of Calif.

[73] Assignee: Hewlett-Packard Company, Palo Alto, Calif.

[21] Appl. No.: 08/985,307

[22] Filed: Dec. 4, 1997

[51] Int. Cl.[6] ............................................. A61B 5/00
[52] U.S. Cl. ...................... 600/573; 600/575; 600/583; 606/181
[58] Field of Search ................... 600/573, 575, 600/578, 583, 584; 606/181, 182

[56] References Cited

U.S. PATENT DOCUMENTS

| | | | |
|---|---|---|---|
| 2,061 | 4/1841 | Osdel | 606/181 |
| 55,620 | 6/1866 | Capewell | 606/181 |
| 1,135,465 | 4/1915 | Pollock | 606/181 |
| 3,030,959 | 4/1962 | Grunert | 128/329 |
| 3,358,689 | 12/1967 | Higgins | 128/329 |
| 4,139,011 | 2/1979 | Benoit et al. | 128/329 |
| 4,203,446 | 5/1980 | Hofert et al. | 128/329 |
| 4,207,870 | 6/1980 | Eldridge | 128/766 |
| 4,230,118 | 10/1980 | Holman et al. | 128/314 |
| 4,442,836 | 4/1984 | Meinecke et al. | 128/314 |
| 4,449,529 | 5/1984 | Burns et al. | 128/314 |
| 4,469,110 | 9/1984 | Slama | 128/770 |
| 4,535,769 | 8/1985 | Burns | 128/314 |
| 4,577,630 | 3/1986 | Nitzsche et al. | 128/314 |
| 4,712,548 | 12/1987 | Enstrom | 128/314 |
| 5,133,730 | 7/1992 | Biro et al. | 606/182 |
| 5,196,025 | 3/1993 | Ranalletta et al. | 606/182 |
| 5,318,583 | 6/1994 | Rabenau et al. | 606/182 |
| 5,318,584 | 6/1994 | Lange et al. | 606/181 |
| 5,510,266 | 4/1996 | Bonner et al. | 436/43 |
| 5,554,166 | 9/1996 | Lange et al. | 606/182 |
| 5,571,132 | 11/1996 | Mawhirt et al. | 606/167 |
| 5,613,978 | 3/1997 | Harding | 606/181 |
| 5,632,410 | 5/1997 | Moulton et al. | 221/79 |

FOREIGN PATENT DOCUMENTS

| | | | |
|---|---|---|---|
| 0630609A2 | 12/1994 | European Pat. Off. | A61B 5/14 |
| WO 86/05966 | 10/1986 | WIPO | A61B 10/00 |

OTHER PUBLICATIONS

Softclix ®, "Lancet Device from the Makers of Accu–Chek ® Systems", (Product), PP. (3 pages), Becton Dickinson & Co., Franklin Lakes, New Jersey, 1996.

One Touch ® Profile™ "Diabetes Tracking System", Owner's Booklet, (Product), pp.31–33, LifeScan Inc., Jun. 1995.

Glucometer Elite ®, "Diabetes Care System", User's Guide, (Product), PP. (3 pages), Miles Inc. Elkhart, IN, Dec. 1994.

Primary Examiner—Robert L. Nasser
Assistant Examiner—Charles Marmor, II

[57] ABSTRACT

A blood sampling apparatus for sampling blood from the skin of a patient for analysis. The apparatus includes a cartridge and a housing with a driver. The cartridge has a cartridge case, lancet, and a compartment associated with the cartridge case for receiving blood. The lancet is housed in the cartridge case and operatively connected thereto such that it is drivable to extend outside the cartridge case through a lancing opening for lancing the skin to yield blood. The housing has a driver for urging the lancet to extend outside the cartridge case. During lancing, the cartridge is preferably detachably held in the housing such that the cartridge can be disassociated from the driver after sampling blood.

32 Claims, 15 Drawing Sheets

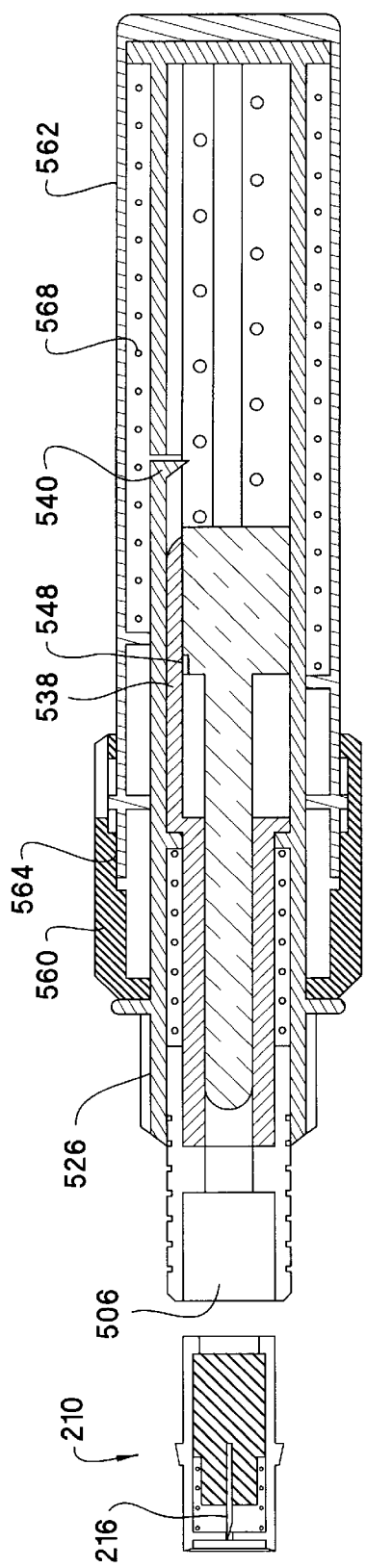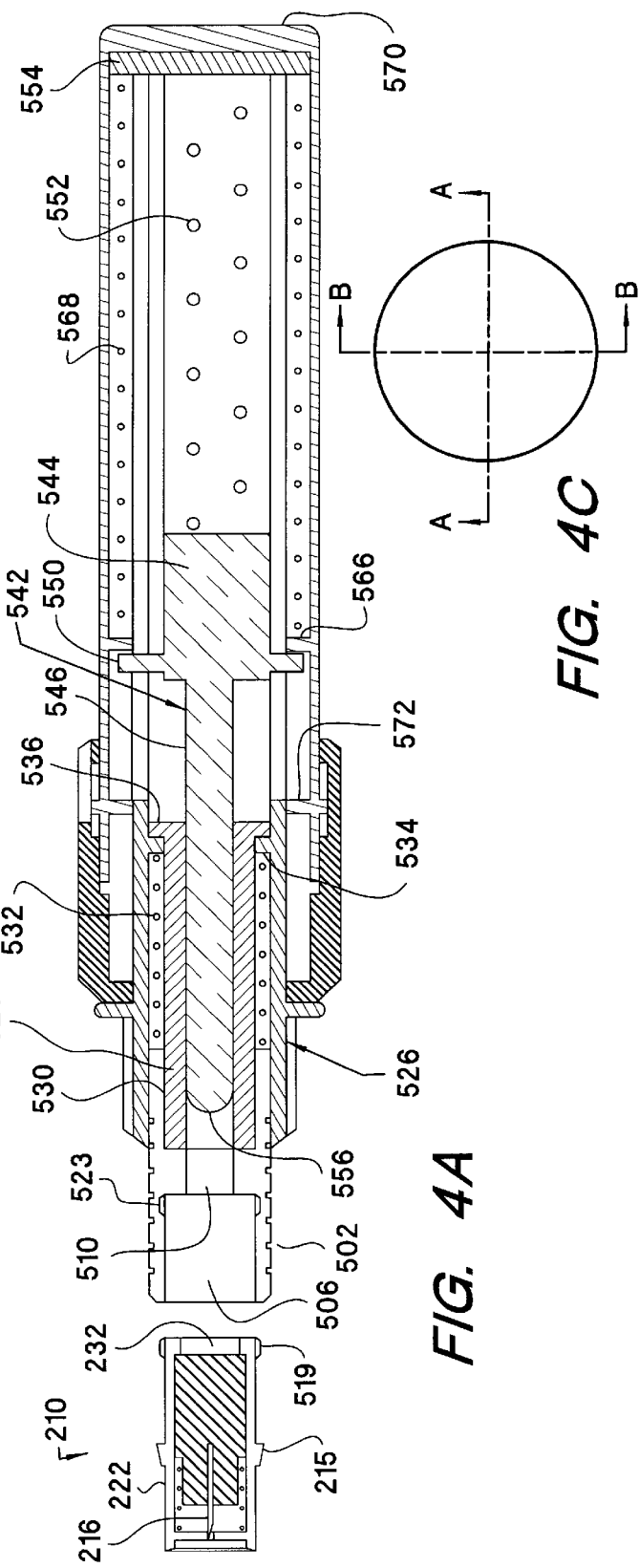

INTEGRATED SYSTEM AND METHOD FOR SAMPLING BLOOD AND ANALYSIS

FIELD OF THE INVENTION

The present invention relates to techniques for obtaining and analyzing blood samples, and more particularly to systems with which a user can conveniently self-administer to sample blood for analysis.

BACKGROUND

The analysis and quantification of blood components is an important diagnostic tool for better understanding the physical condition of a patient. Since adequate noninvasive blood analysis technology is not currently available, blood samples still need to be obtained by invasive methods from a great number of patients every day and analyzed. A well known example of such needs is self monitoring of glucose levels by a diabetic individual, e.g., performed at home. Many products for self monitoring of blood glucose levels are available commercially. Upon doctors' recommendations and using such products, patients typically measure blood glucose level several (3–5) times a day as a way to monitor their success in controlling blood sugar levels. For many diabetics, the failure to test blood glucose regularly may result in damage to tissues and organs, such as kidney failure, blindness, hypertension, and other serious complications. Nevertheless, many diabetics do not measure their blood glucose regularly. One important reason is that the existing monitoring products may be complicated, inconvenient, and painful, requiring a pin-prick every time a measurement is made. Furthermore, these products require some skill, dexterity, and discipline to obtain useful measurements.

Today, a diabetic patient who needs to monitor and control blood glucose levels typically carries the following paraphernalia: (1) a supply of disposable lancets, (2) a reusable lancing device which accepts the lancets, (3) an electronic glucose meter (glucometer), (4) a supply of disposable glucose test strips for the meter, and (5) tools for insulin injection (insulin, disposable hypodermic needles, and a syringe). These items may be carried in the form of a kit, which may also contain (6) a variety of control and calibration strips to assure the accuracy of the meter and the measurement. Examples of devices for monitoring blood glucose include GLUCOMETER ELITE glucose meter, Miles Inc. Elkhart, Ind., and ONE TOUCH PROFILE glucose meter, Lifescan Inc., Milpitas, Calif.

Using a typical glucose meter and lancing device, the sampling and measurement process is generally as follows. First, the user prepares the meter for use by removing a test strip from a protective wrapper or vial and inserting the test strip in the meter. This simple process requires some dexterity, since the test strips are very small, flexible, and can be damaged by accidentally touching the active sensing region. The glucose meter may confirm the proper placement of the test strip and indicate that it is prepared for a sample. Some glucose meters also may require a calibration or reference step at this time. Next, the patient cleans his finger when he intends to use the lancet—the finger is the preferred place for routine sampling, because it is an easily accessible place for most people. The user prepares the lancing device by (1) removing a cover from the lancing device, (2) placing a disposable lancet in the lancing device, (3) removing a protective shield from the sharp lancet tip, (4) replacing the cover, and (5) setting a spring-like mechanism in the lancing device which provides the force to drive the lancet into the skin. These steps may happen simultaneously, e.g., typical lancing devices set their spring mechanisms when one installs the lancet. The user then places the lancing device on the finger. (The density of nerve endings decreases toward the lateral edges of the fingertips; thus, slightly lateral locations are preferred to the fingertips.) After positioning the lancing device on the finger, the user presses a button or switch on the device to release the lancet. The spring drives the lancet forward, creating a small wound.

After lancing, a small droplet of blood may appear spontaneously at the lancing site, usually 2–20 $\mu$l in volume. If no blood sample appears spontaneously, the patient may "milk" the finger by massaging or squeezing it slightly and thereby promoting blood flow from the wound. In either case the user examines the droplet of blood, judges by eye and experience whether the size of the sample is adequate for the chosen test strip (different test strips require different sample volumes). If adequate, the user quickly places the blood sample on a test strip (held in the glucose meter) according to manufacturer's instructions. Typically, the user inverts the finger to create a pendant drop and touches the drop (not the finger) to an active region on the test strip that absorbs the blood. The action is difficult because inverting the finger over the test strip occludes the view of both the drop and the active region of the test strip. Furthermore, it is difficult to control the separation between the finger and the test strip which may be only a millimeter. Certain types of strip may require blotting and rubbing in a particular way. Another type of test strip draws the sample into the active region by capillary action. With this type, the user brings the sample in contact with a small opening on the test strip, and capillary action draws the sample volume into the test strip. Both types of strips (absorbent blots and capillaries) require that adequate sample volumes of blood exist on the finger before transferring the sample to the strip. One cannot apply more drops after the first application. This is because the principle of glucose measurement methods using current glucose meters depends on the rate of change in a chemical reaction, and the addition of additional sample confounds that rate and thus the calculation of glucose concentration. For convenience to the patient (user), it is desirable to have the entire droplet wick away from the finger onto the test strip, leaving the finger mostly free of blood. This is easier to accomplish with the capillary-fill test strips. The GLUCOMETER ELITE device has capillary-fill type test strips which require a few microliters of sample, only some fraction of which contacts the active sensor region.

After blood has been transferred to the test strip, the glucose meter then measures the blood glucose concentration (typically by chemical reaction of glucose with reagents on the test strip). Such blood glucose measurements permit the diabetic to manage his glucose levels, whether that be to inject a corresponding dose of insulin (generally Type I diabetic) or using a protocol established with his physician to modify his diet and exercise (Type I or Type II diabetic). Used lancets and test strips are removed and discarded (or kept for subsequent disposal in a hazardous waste container kept elsewhere). Any extra blood is cleaned from the equipment and the wound site, and all pieces of apparatus are stored for future use. The entire process usually takes a few minutes.

With the currently available blood glucose monitoring technology, a new lancet and test strip are used every time. The lancet and test strip are separate items, often purchased from different manufacturers. Furthermore, both are protected by a package or a protective shield, which must be removed before use, adding the requirement for dexterity. Because both are exposed to blood (considered a bio-hazard) they require careful or special disposal.

Each lancet prick causes pain. Among other considerations, pain from the lancet corresponds to the size of the wound, for a given location on the finger. A small lancet wound, which may cause less pain, may not provide enough blood for a sample, while a large wound may produce considerable pain and may clot slowly, causing great inconvenience to the user, who must take great care not to smear the leaking blood everywhere—clothes, work surfaces, glucometer, etc.—for some time thereafter.

From the above, it is clear that the conventional technique for blood sampling and analysis requires dexterity. Dexterity is required to load strips in a glucometer (unwrapping and inserting), as well as for positioning a small droplet onto the sensor surface of a test strip. Sample droplets are a few millimeters across and must be placed on similarly sized area of the test strip. This can be especially difficult for a weak, chronic or elderly diabetic patient, whose motions may be unsteady, vision compromised, or judgment impaired. Thus, the above prior systems are inconvenient and unpleasant to use. These shortcomings reduce the level of compliance of patients who need to perform these measurements assiduously.

Although the current designs of the lancing devices limit the range of travel of the lancet so that they cannot penetrate too deeply into the skin, much variation in penetration depth of the lancets can result due to different placement and handling of the devices by the user. For example, if the user presses a lancing device firmly against the skin, the skin is taut and the lancet penetrates deeply and therefore more painfully. If the user holds the lancing device against the skin lightly, the skin is loose and more compressible than a taut skin. In this case, when the lancet moves against the skin it first creates a shallow depression before penetrating the skin, thus resulting in a shallow wound. With existing lancing tools, it is possible for the user to vary the lancing depth from almost nil (no wound, no blood sample, and probably no pain) to very deep (~1 mm deep wound, spontaneously flowing blood, and considerable pain).

The quality of the measurement depends on careful placement of a small drop of blood, typically a few millimeters in diameter, against a similarly small target (test strip or sample hole). With glucometers of prior technology, the exact location of the blood droplet or the wound might be obscured from view by the bleeding finger, which is inverted to deposit the blood on the strip. Such uncertainty about the position of the blood droplet can lead to less than desirable accuracy in the measurement.

Therefore, it is desirable to devise techniques of blood extraction and measurement which promote patient compliance. What is needed are improved devices and methods for sampling and analyzing blood that require less thought, less exertion, less dexterity, and result in less pain.

SUMMARY

This invention provides techniques for extracting a sample of human blood for the measurement of one or more of its constituents, such as might be used for routine monitoring of a chronic condition. The techniques of the present invention simplify the extraction and transfer of the blood sample, and reduce the unpleasantness and inconvenience of the process. The techniques can be advantageously used in, for example, blood glucose monitoring as explained above.

In one aspect of the present invention, a blood sampling apparatus is provided for sampling blood from the skin of a patient. The apparatus includes a cartridge. An embodiment of the test cartridge includes a cartridge case and a lancet. Associated with the cartridge case is a compartment for containing blood sampled. Preferably, the property of blood can be analyzed in the cartridge. The lancet has a tip for piercing the skin and is operatively connected for motion to the cartridge case in which it is housed. The lancet can be pushed to extend its tip outside the cartridge case for lancing the skin to yield blood. A driver is used to push the lancet for lancing.

In an embodiment of the present invention, the technique of sampling blood utilizes a single unit for lancing and measurement (vs. separate lancers and meters as in prior methods) to significantly reduce the assortment of devices and supplies the user must carry. The glucometer of the present invention can accept a pre-loaded number of test cartridges (with lancets) that are ready for use. The lancet and the analysis site for blood are in the same test cartridge, further improving the convenience of use. Using the blood sampling and analysis devices of the present invention, unlike the procedures of prior techniques, the long list of steps required is significantly reduced. For example, there is no need to separately remove the lancet from its protective shield and removing a test strip from its protective packaging. The need for handling an actuating device separate from the glucometer is obviated. Further, the act of inserting the test cartridge into the glucometer in the present invention is significantly simpler than the prior methods of preparing a glucose meter for use. In fact, in an embodiment of the present invention, the process of sampling and analyzing blood from a finger, not including the steps for preparing the finger before sampling blood, is reduced to inserting a test cartridge into position in the glucometer, cocking the actuator and releasing it to prick the finger, maintaining the lanced finger at the sample port to deposit the blood droplet from the lanced wound, removing the lanced finger from the glucometer, and pushing the right buttons to control the electronics of the glucometer. All these steps can be performed from start to finish without having to put down the glucometer and pick up another device, which is impossible with prior techniques.

Furthermore, in preferred embodiments of the glucometer of the present invention, ergonomic features such as finger rests, magnifying lens with graticule, lancet drivers with controlled force of lancing, absorbent surface for cleaning the lanced finger of excess blood can be provided. These ergonomic features significantly improve the convenience and reduce the pain and discomfort of blood sampling and analysis.

BRIEF DESCRIPTION OF THE DRAWINGS

The following figures are included to better illustrate the embodiments of the apparatus and technique of the present invention. In these figures, like numerals represent like features in the several views.

FIG. 4A shows a sectional view of a blood sampling device suitable for use with a bar-shaped test cartridge in accordance with the present invention, FIG. 4B shows a sectional view of the blood sampling device of FIG. 4A taken on a sectional plane of at a right angle thereto.

FIG. 4C shows a schematic cross-section relating the sectional views of FIGS. 4A and 4B.

DETAILED DESCRIPTION OF THE INVENTION

In one aspect of the invention, an apparatus having a lancet is provided to sample blood safely and conveniently. In preferred embodiments, blood can be sampled and analyzed conveniently, and the lancet can be installed and disposed of safely without the user having to touch the lancet by hand. Ergonomic features can be included to enable a user with impaired dexterity to safely and conveniently sample and analyze blood.

Cartridges

Blood sampling apparatuses and lancing devices with cartridges can be designed and made for a wide variety of cartridges in accordance with the present invention. For example, a few of the cartridge embodiments that can be used with the lancing devices of the present invention are disclosed in copending U.S. patent application entitled "Lancet Cartridge for Sampling Blood," Docket Ser. No. 10971750-1, filed on the same day and commonly assigned to the same assignee as the present application. Further, a plurality of cartridges can be stored in a cassette and be used in a lancing device. Examples of cassettes of cartridges suitable for application with the present lancing devices are disclosed in copending U.S. patent application entitled "Cassette of Lancet Cartridges for Sampling Blood," Docket Ser. No. 10971749-1, filed on the same day and commonly assigned to the same assignee as the present application. Said copending applications are incorporated by reference in their entirety herein. These cartridges and cassettes described in said copending applications and here are given as illustrative examples. It is to be understood that other variations can be used with the systems of the present invention.

An example of a test cartridge suitable for use in the present invention includes a lancet, a cartridge case with an opening through which the lancet can protrude, and a test area (i.e., analytical region) associated with the test cartridge case for analysis of blood. The lancet is mounted in the cartridge case in such a manner that (1) it can move with respect to the cartridge case and extend through the opening when forced by a separate actuator, and (2) when no actuating force acts on the test cartridge, the lancet has a natural resting position entirely inside the cartridge case. Analysis can be done in the test area. An alternative is that a chamber can be used to store blood to be transferred to a separate analytical area from the test area. Although lancing with test cartridges are described in detail herein as illustrative examples, it is noted that the present invention is also applicable to "storage cartridges" in which blood is stored after sampling, without analytical function in the cartridges.

Flat Cartridges

Figure 1A:
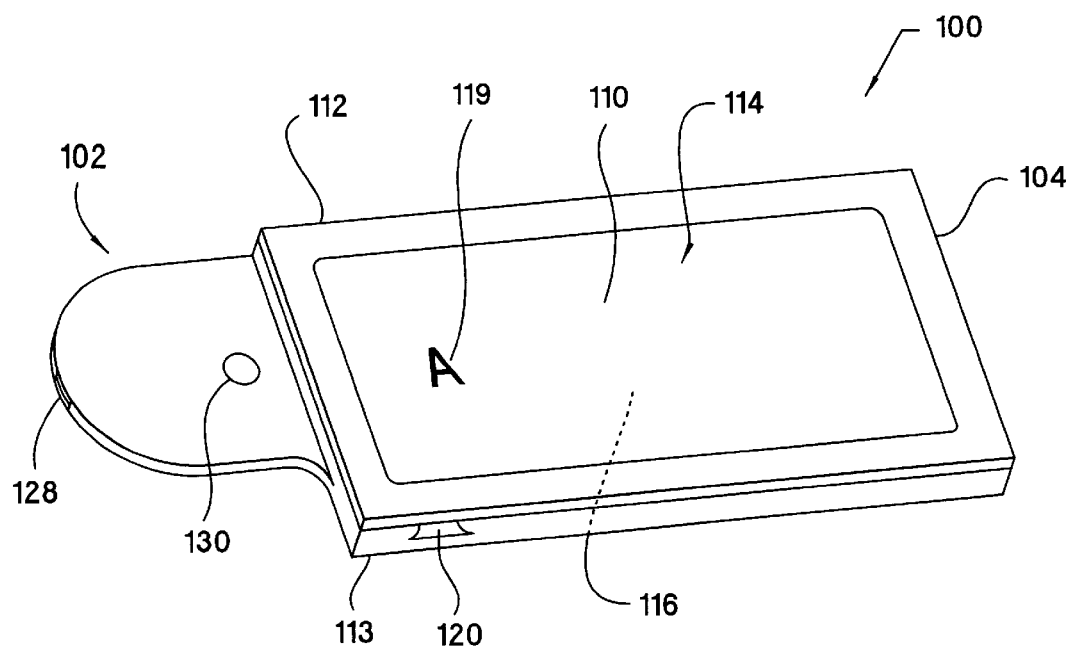
FIG. 1A shows an isometric view of an embodiment of the flat type of test cartridge of the present invention.
Figure 1B:
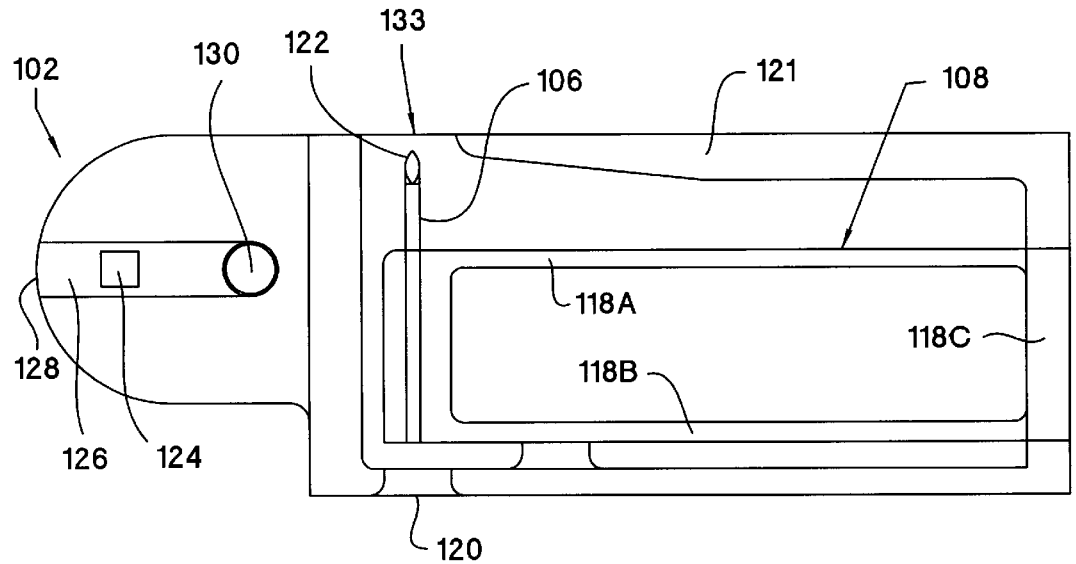
FIG. 1B shows a plan view of the test cartridge of FIG. 1A.

FIG. 1A shows an isometric view and FIG. 1B shows a plan view of an embodiment of a test cartridge that can be included in a cassette of the present invention. The test cartridge of FIG. 1A and FIG. 1B has a generally flat appearance, thus allowing many test cartridges to be stacked together conveniently for storage in the cassette. However, it is to be understood that other non-flat-shaped cartridges can also be used, so long as they can be stacked. For example, the cartridge can have two opposite surfaces each having a cross section that is curved, wavy, etc. to match the other surface. A test portion 102 protrudes from one side of the test cartridge 100. The test cartridge 100 can include a material for analysis of blood (see infra). The device 100 is referred to as a "test cartridge" because strips for analysis of blood in prior glucose meters are called "test strips" in the technical field. The test cartridge 100 has a cartridge case 104 integrally connected with the test area 102. A lancet 106 is connected to a cantilever lancet frame 108. The side of the cantilever lancet frame 108 remote to the lancet 106 is affixed to the cartridge case 104 whereas the side of the cantilever frame 108 near the lancet 106 is not affixed to the cartridge case 104. Thus, the lancet is operatively connected in the cartridge case 104 for movement. A covering 110 which has an absorbent material (for absorbing residual blood from the wound after lancing and testing) covers a surface preferably the top surface) of the cartridge case 104. As used herein, the term "top surface" when used in connection with the generally flat test cartridge refers to the surface that is exposed for the most convenient access when the test cartridge is installed in association with a driver for lancing. Preferably, the top surface will face the same direction as displays of a glucometer when the test cartridge is loaded (or deployed) in the glucometer. Preferably, the cartridge case has a top face 114 on a top plate 112 and a bottom face 116 on a bottom plate 113 that are generally flat such that cartridges of this kind can be stacked one on top of another, and such that the covering material 110 can be conveniently used for wiping blood from the skin after lancing.

In this embodiment, as shown in FIG. 1B, the lancet 106 is mounted on a two-armed cantilever frame 108, the arms 118A, 118B of the cantilever frame 108 being about 20 mm long. A separate mechanism (e.g., an actuator rod not shown in the figures) inserted through a push port (or access hole) 120 can push the lancet 106 forward by acting against the part of the cantilever frame near the blunt end of the lancet 106. The lancet 106 at its distal end remote from the blunt end has a sharp tip 122 for penetrating the skin. As used herein, the term "distal" refers to a location or direction towards the skin to be lanced. The term "proximal" refers to a location or direction that is opposite to "distal," near to the hand that is handling the lancing device. The cantilever structure causes the lancet 106 to move in a generally straight direction (parallel to the lancet axis) with negligible curving or sideways motion, in order to pierce the skin with minimal tearing. In an at-rest state the lancet 106 resides about 0.5 mm proximal of the outside surface of the cartridge to prevent unwanted injuries. The lancet 106 is preferably 0.35 mm in diameter or smaller in order to not inflict a large wound.

When pushed, i.e., actuated, the lancet 106 extends through the cartridge wall through an exit port 133. The lancet 106 will extend out of the distal side of a lancing device through lancing hole 176, see FIG. 7. The cantilever arms 118A and 118B have a resilient property that, when the cantilever arms are bent, a tension develops to return (or spring) the lancet 106 to its at-rest position after lancing the skin and the actuating force on the lancet 106 is withdrawn (e.g., the actuator rod that inserts into the port 120 withdraws). The cartridge case 104 has a port 120 on the side of the cartridge case near to the blunt end of the lancet 106 for an actuator arm or rod (e.g., a push rod) to be inserted to push the lancet, thereby extending the lancet tip out the cartridge case 104. The maximal total travel of the lancet may be a few millimeters, limited by the interference (contact) of the cantilever lancet frame 108 and cartridge wall 121. The exact limit of travel of the lancet, which is important to minimize pain and injury, may be controlled by a mechanism which pushes the cartridge frame (which will be described later in the following). Each cartridge 100 may have an identifying mark 119 on the top surface 114 or absorbent cover 110. The identifying mark 119 can indicate the number of the cartridge (in a batch) or a special function (e.g., for a calibration cartridge). Further, special function cartridges can have a different color.

FIG. 1B is a plan view of the cartridge showing the test portion 102 and the lancet structure. The test portion 102 includes a test compartment (or test area) 124 depicted as a small square. As used here, the term "test compartment" refers to a space into which blood can pass and in which the property of the blood is analyzed. A capillary passageway 126, for example, allows communication between a port (or entrance) 128 from which blood enters the test area 124. A vent hole 130 a distance (e.g., about 5 mm) away from the entrance 128 to the capillary, to the opposite side of the test area 124, terminates the capillary force to halt the filling of the capillary volume after pulling a blood sample over the active test area 124. As an alternative, a compartment without analytical capability can be used in place of a test area for storing blood. Such a compartment may have anticoagulants to prevent the blood from clotting.

In a preferred embodiment (although not clearly shown in FIGS. 1A and 1B), the test cartridge 100 has electrical contacts that allow for electrical communication with an instrument that processes a measurement (and perhaps controls the analysis) of an analyte (e.g., glucose) on the active test area. Such electrical contacts can be placed at a variety of locations on the test cartridge. Placing the contacts on the bottom (i.e., the side facing oppositely from the covering 110) permits a simple design and a simple interface to an instrument.

For analysis of the blood sampled, the test area 124 can contain chemicals that react with components of the blood samples. For example, enzymes that react with glucose can be present. The test area may also contain reagents that react with the iron present in the blood hemoglobin. Techniques, including electrochemical or spectroscopic techniques, that can be used for analysis of blood can be incorporated in the test cartridge 100. Examples of applicable analysis techniques can be found in, e.g., Tietz, Norbert W., Textbook of Chemical Chemistry, Chapter 6, pp 784–807, W. B. Saunders Co., Philadelphia, Pa., 1986, which are incorporated by reference herein. Test strips for analyzing glucose, pH, iron, and other common blood qualities are known in the art. For example, ONE TOUCH PROFILE diabetes tracking system commercially available from Lifescan Inc., Milpitas, Calif. 95035 has a unit that utilizes a strip for analyzing blood glucose and has an electronic system for displaying the result of analysis.

The top plate 112 or the top surface 110 may have a variety of useful markings that indicate which test cartridge is in use (in the case that the test cartridge is one out of many from a stack of test cartridges), and indication of batch or lot number of manufacture (for quality control and calibration), or that the cartridge is a special-purpose cartridge (e.g., for checking or calibration).

Figure 2:
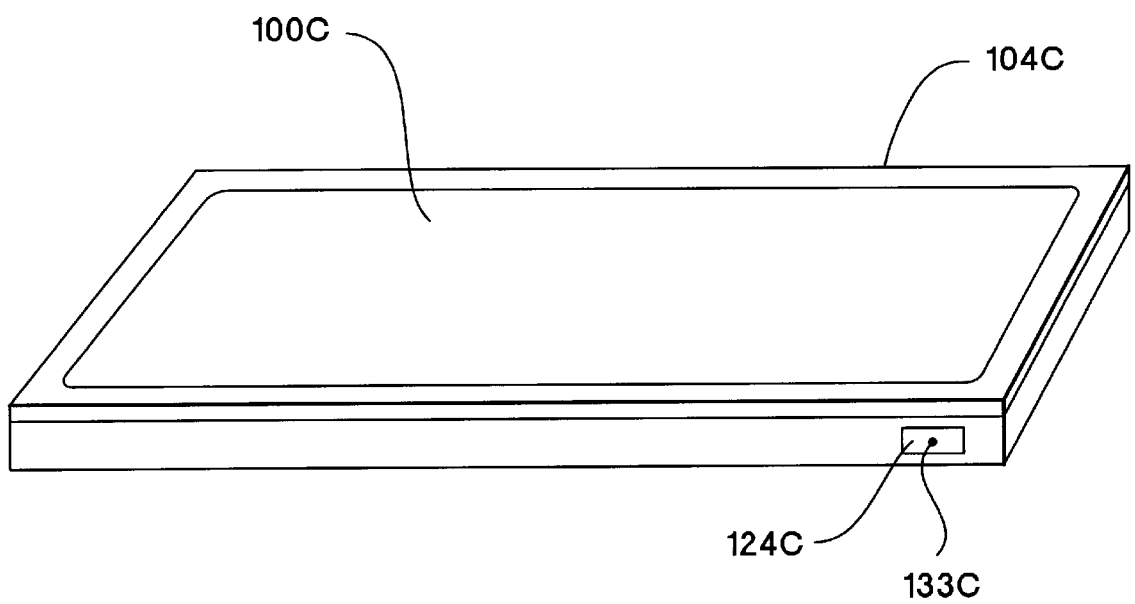
FIG. 2 shows an isometric view of another flat type test cartridge of the present invention.

Other embodiments of flat cartridges are also applicable in accordance with the present invention, such as a test cartridge with the test area 124 protruding at a different side of the lancet area, or having a test area that resides directly neighboring the lancet 106 near the tip 122, so that the entrance (i.e., sample port) 128 to the capillary volume 126 and the exit port 133 for the lancet 106 are nearly coincident. This latter design enables the patient to lance the skin, and have the sample port for the test strip co-located for immediate filling. An example of such an embodiment is shown in FIG. 2. The test cartridge 100C has a test area 124C that is at the immediate vicinity of the lancet exit port 133C, which in this embodiment is a hole. The test area 124C can be a sensing surface surrounding the lancet exit port 133C. Preferably the test area 124C is set back slightly from the distal side of the cartridge case 104C so as to avoid inadvertent contact with skin or other objects. When the skin is lanced and a drop of blood appears, the drop of blood can reach beyond the set back distance to contact the test area 124C.

Bar-Shaped Cartridges

Figure 3A:
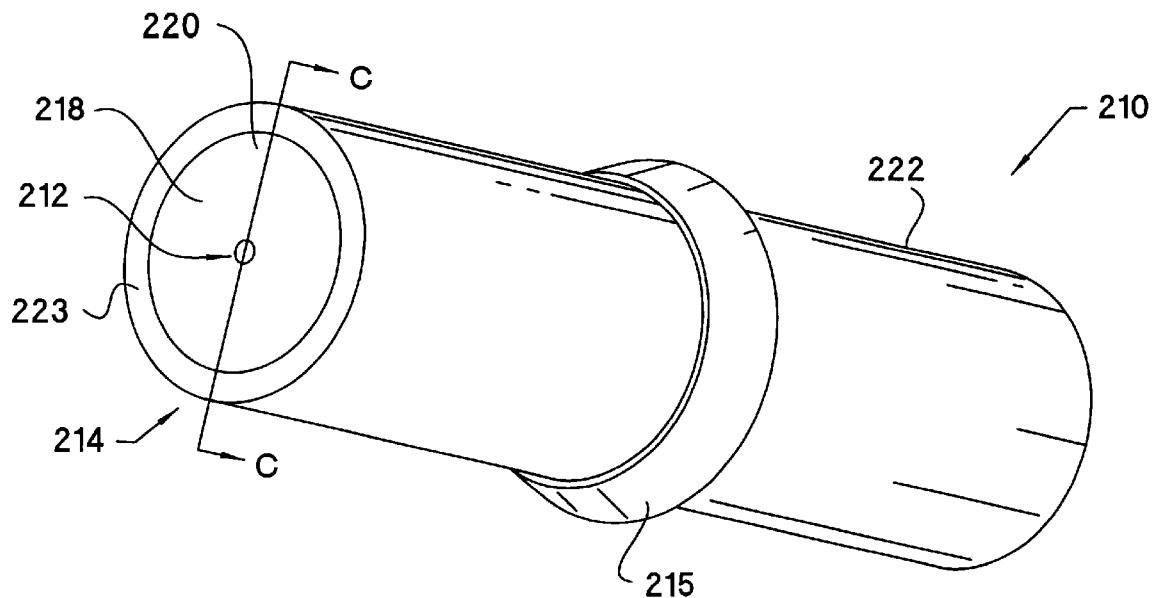
FIG. 3A shows an isometric view of a bar-shaped test cartridge of the present invention.
Figure 3B:
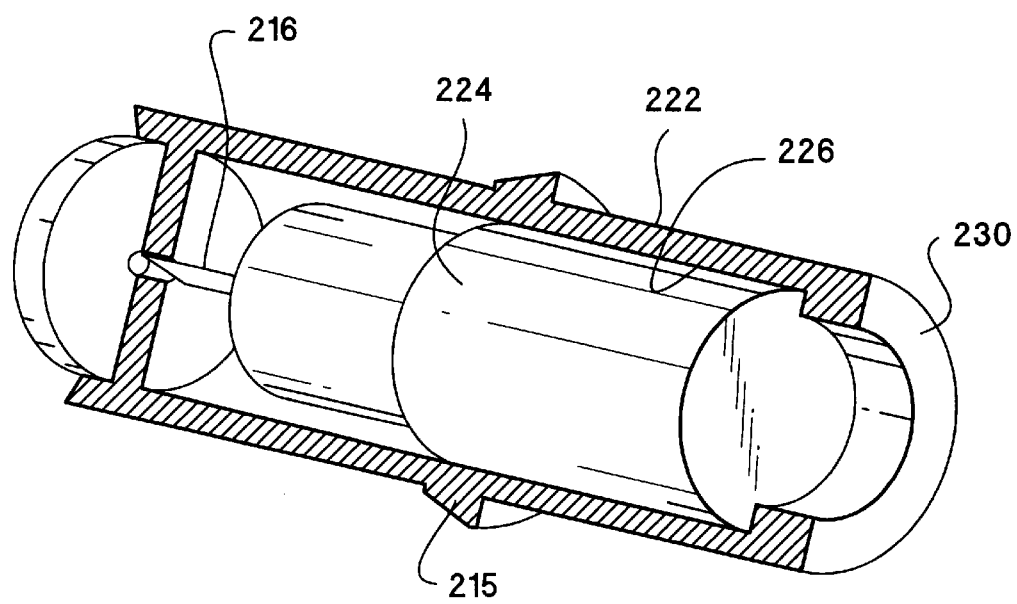
FIG. 3B shows an exploded isometric view in portion of the test cartridge of FIG. 3A.

FIGS. 3A to 3D show an embodiment of a bar-shaped cartridge that can be included in a cassette. The test cartridge 210 has a lancet and a blood analyzer, i.e., sensor (such as a blood chemistry test strip that can determine glucose level) and can be mounted easily into a driving instrument (driver). The overall lancing device operates with the test cartridge to gather a blood sample in a single operation and simplifies the measurement procedure. FIG. 3A shows an isometric view of the embodiment of the test cartridge 210, about 6 mm in diameter and 15–20 mm in length. FIG. 3B shows an isometric view, cut-out in portion, of the test cartridge 210 along plane C—C of FIG. 3A. For comparison, the size and shape is similar to that of the ULTRAFINE lancets of the Becton-Dickinson Co. with a 29 AWG needle. It is noted that, although the bar-shaped test cartridge 210 has, preferably, a round cross-sectional shape, it can also have other regular cross-sectional shapes, such as oval, square, rectangle, rhombus, triangle, etc. An aperture 212 (or lancet exit hole) is located at a distal end 214 of the test cartridge 210. A lancet 216 is housed at rest inside the test cartridge 210 proximal of (i.e., beneath if considering the distal end as facing upwards) the aperture 212, which has a diameter slightly larger than the lancet 216 (~0.35 mm diameter). The lancet 216 can pass through the aperture 212 when actuated for lancing. Herein, when referred to a bar-shaped test cartridge, "top," and "up" refer to a direction or location towards the skin to be lanced, i.e., towards the distal end. The material 218 around the aperture can be an absorbent material which serves to soak up blood after lancing. The absorbent material, or the surface beneath it, can also serve as the active test area 220 for measurements of blood characteristics, such as glucose level. As in existing glucose measurement techniques, a chemical reaction occurs when blood contacts the test area 220, and thus, for example, indicates the presence and amount of glucose. The test area 220 can generate an electrical signal that is conducted from the test area 220 (preferably via conductors molded into the case) to electrical contacts (not shown) on the cartridge case 222. The test cartridge case 222 has a lip 223 protruding slightly out distally at the distal end 214. The protruding lip 223 results in a small void area protecting the test area 220 from being inadvertently touched and help to provide uniform tautness to the skin. As used herein, the meaning of the term "compartment" when referred to the space for receiving blood also can include the space encircled by the lip 223. FIG. 3B is a projected sectional view in portion of the cartridge, showing the cartridge case 222, the lancet 216, and the absorbent material 218 distal to the lancet 216 when at rest. The lancet 216 is mounted on a cylindrical lancet mount 224. The cartridge case 222 has a cylindrical internal wall 226 upon which the lancet mount 224 can slide.

Figure 3C:
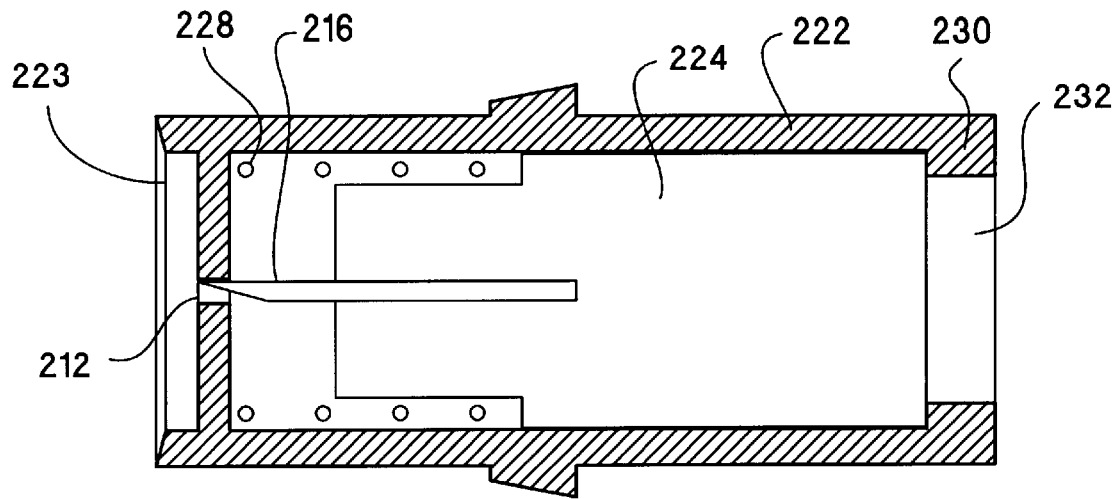
FIG. 3C shows a sectional view along the axis of the bar-shaped test cartridge of the present invention.
Figure 3D:
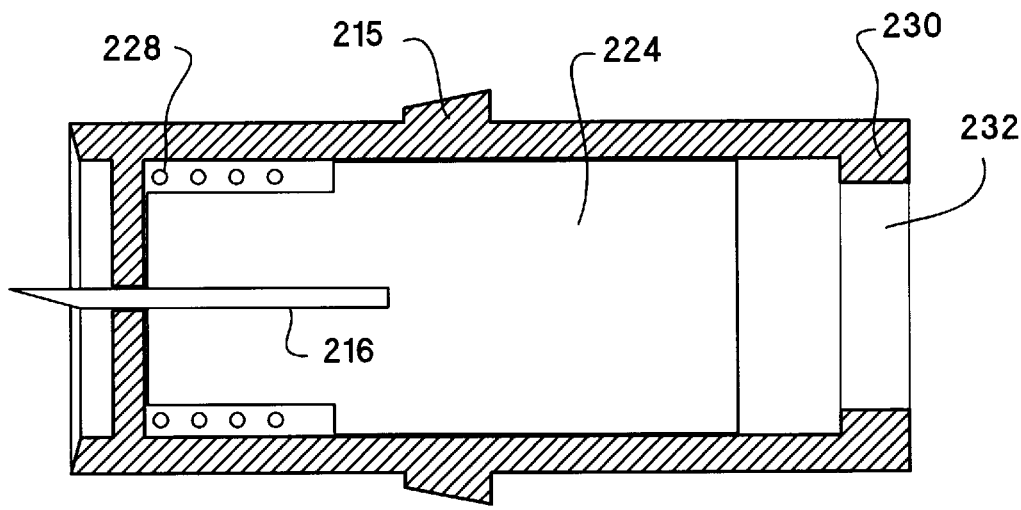
FIG. 3D shows a sectional view of the test cartridge of FIGS. 3A–3B, showing the lancet extended for lancing.

FIGS. 3C and 3D are sectional views of the test cartridge 210 along the plane C—C of FIG. 3A. Shown in FIGS. 3C and 3D (but not in FIG. 3B for clarity) is a retaining spring 228 which compresses the lancet mount 224 against the bottom 230 of the test cartridge 210. A large bore 232 on the bottom 230 of the cartridge case 222 permits an external actuator (not shown in FIGS. 3A to 3D) to extend through to act on the lancet mount 226. FIG. 3C shows the test cartridge 210 at rest, with the lancet 216 residing beneath the aperture 212 and the absorbent surface 218. When an external actuator (not shown in FIG. 3) acts through the bottom bore 232 against the lancet mount 224, the cartridge spring 228 is compressed and lancet 216 will emerge through the aperture 212 where it can pierce a patient's skin. See FIG. 3D. When the actuating force is removed, e.g., by withdrawal of the actuator, the resilient nature of the cartridge retaining spring 228 returns the lancet 216 to the at-rest position inside the cartridge case 222. In this manner, the lancet 216 is only exposed during lancing. Therefore, the user is protected against unintentionally inflicted wounds and scratches, and also from exposure to the contaminated lancet. With prior technology, accidental lancet pricks can occur more easily than with the cartridges of the present invention. It is to be understood that although test cartridges with analytical regions are described in detail herein, the lancing device of the present invention is equally applicable to cartridges that do not have an analytical region, such as a cartridge having a chamber for storing blood after sampling. Such storage cartridges, whether the flat type or the bar-shaped type, will be obvious to a person skilled in the art in view of the present disclosure. One example would be a cartridge having a storage chamber connected by a channel to the blood inlet port in the afore-mentioned test cartridges, without the reagents that can interact with the blood.

Device for Reproducible Lancing

Lancing devices having a driver driving a cartridge can be used for lancing. In the embodiment shown in FIGS. 4A and 4B, the lancing device has a generally elongated shape. FIGS. 4A and 4B show sectional views of the lancing device along the elongated dimension. The sectional views are sections through different angles (right angle to each other), so that they reveal different aspects of the interior parts. FIG. 4C is a schematic representation of the cross-section of the lancing device, showing line A—A as the plane for the sectional view of FIG. 4A and line B—B as the plane for the sectional view of FIG. 4B. This lancing device embodiment permits adjustment of the depth of the lancet and adjustment of the preload applied to the skin before lancing. In FIGS. 4A and 4B, the test cartridge 210 is shown removed from the lancing device 500 for clarity.

The lancing device 500 has a cartridge holder 502 with a recessed section 506 that accepts a bar-shaped test cartridge 210, similar to the bar-shaped test cartridge of FIG. 3A and FIG. 3B. The test cartridge 210 can be mounted in the cartridge holder 502 in a reproducible manner. That is, the test cartridge 210 can be repeatedly mounted and removed from the cartridge holder 502 and still attain the same position relative to the cartridge—by locating against a cartridge flange 215 that is molded onto the case 222 of the test cartridge 210. The bore 232 in the bottom of the test cartridge 210 is exposed to the interior of the lancing device through a bore 510 in the cartridge holder 502.

If the test cartridge 210 has an active test area for analytical measurement, then the test cartridge 210 should preferably also possess electrical contacts 519, which communicate to complementary contacts 523 in the cartridge holder 502. The lancing device 500 can either contain a processor such as CPU of a computer (not shown) or communicates with a CPU that can compute results from the signals received from the test cartridge. Thus, the lancing device 500 becomes part of an entire measurement instrument, which can compute and display results (such as blood glucose concentration).

The cartridge holder 502 can slide freely inside a casing 526. A force adjuster 528 can also slide freely inside the casing 526. The force adjuster 528 has a threaded end 530 that threads into matching threads on the cartridge holder 502. An adjuster spring 532 is compressed between the cartridge holder 502 and a flange 534 on the casing 526. By adjusting the position of the threaded end 530 of the force adjuster 528 relative to the threads on the cartridge holder 502, the degree of compression of the adjuster spring 532 can be adjusted, to apply an outward force on the cartridge holder 502 (and thereby also the force adjuster to which the cartridge holder is threaded). An adjuster flange 536 on the force adjuster 528 restrains the travel of the force adjuster (and cartridge holder 502) relative to the casing 526. Protruding further from the adjuster flange 536 on the force adjuster 528 is a trigger 538, which extends to within a preset distance of a catch 540 on the casing 526 (see FIG. 4B). Inside the casing 526 is a plunger 542 having a larger base 544 and a long, more slender shaft 546. The base 544 has a small recession 548 and two protruding tabs 550. Attached to the plunger base 544 is a driving spring 552 which extends inside the casing 526 to the casing base 554. In equilibrium, the driving spring 552 holds the plunger 542 in the location shown in FIG. 5A (inside the casing) with the tip 556 of the plunger long shaft 546 held at a preset location inside the bore 510 of the cartridge holder 502. Around the casing 526 is a depth adjuster 560 and a cocking tube 562. One end of the cocking tube 562 has threads 564 that match to the threads in the depth adjuster 560. Between the casing 526 and the cocking tube 562 (more specifically between the casing base 554 and the tube flange 566) is a tube spring 568 which applies a compressive force between the casing base 554 and the tube flange 566 on the cocking tube 562. The base (or closed end) 570 on the end of the cocking tube remote from the test cartridge 210 restrains the cocking tube 562 against the casing base 554.

In general, when the cocking tube 562 is pulled back and then released, the catch 540 on the casing 526 locks into the recession 548 on the plunger 546 and compresses the driving spring 552. Pushing the intended site for lancing on the skin to the test cartridge 210 at its distal end compresses the cartridge holder 502 partially into the lancing device 500. Eventually the trigger 538 advances toward the catch 540 which retains the plunger 542 and releases the catch 540 from the plunger 542. As a result, the driving spring 552 drives the plunger 542 distally, thereby forcing (i.e., urging or punching) the lancet of the test cartridge into the skin. Afterwards, in the preferred mode in which the driving spring 552 is a ballistic spring that attaches to the plunger base 544, the driving spring recoils to its resting position and pulls back the plunger, and the lancet retracts into the test cartridge 210.

In order to adjust the preload (which affects the skin tension), the user can rotate the cartridge holder 502 with respect to the casing 526, which causes it to move along the matching threads of the force adjuster 528. Varying the position of the cartridge holder 502 with respect to the force adjuster 528 varies the compression of spring 532. The user can increase or decrease the force on the cartridge holder 502, thereby setting the force at the location where the trigger 538 reaches the catch 540 on the plunger 542. This force is the preload force at the instant of lancing.

In order to further adjust the depth of penetration of the lancet, the user rotates the depth adjuster 560, causing the cocking tube 562 to slide into a new position where it remains fixed with respect to the depth adjuster 560. The location of the cocking tube 562 determines the location of flange 572 on the cocking tube. Flange 572 acts as a limiting stop for the travel of the plunger 542 inside the casing. The lancet 216 can only travel the distance that the plunger pushes it, so setting the limit of travel of the plunger 542 determines how far the lancet 216 can extend out of the test cartridge 210. This is the maximum depth of penetration of lancing.

Alternatively, a conventional driver with a cocking and release mechanism including a release button can be used for driving the test cartridge. Such mechanisms with release buttons are known in the art.

Figure 5:
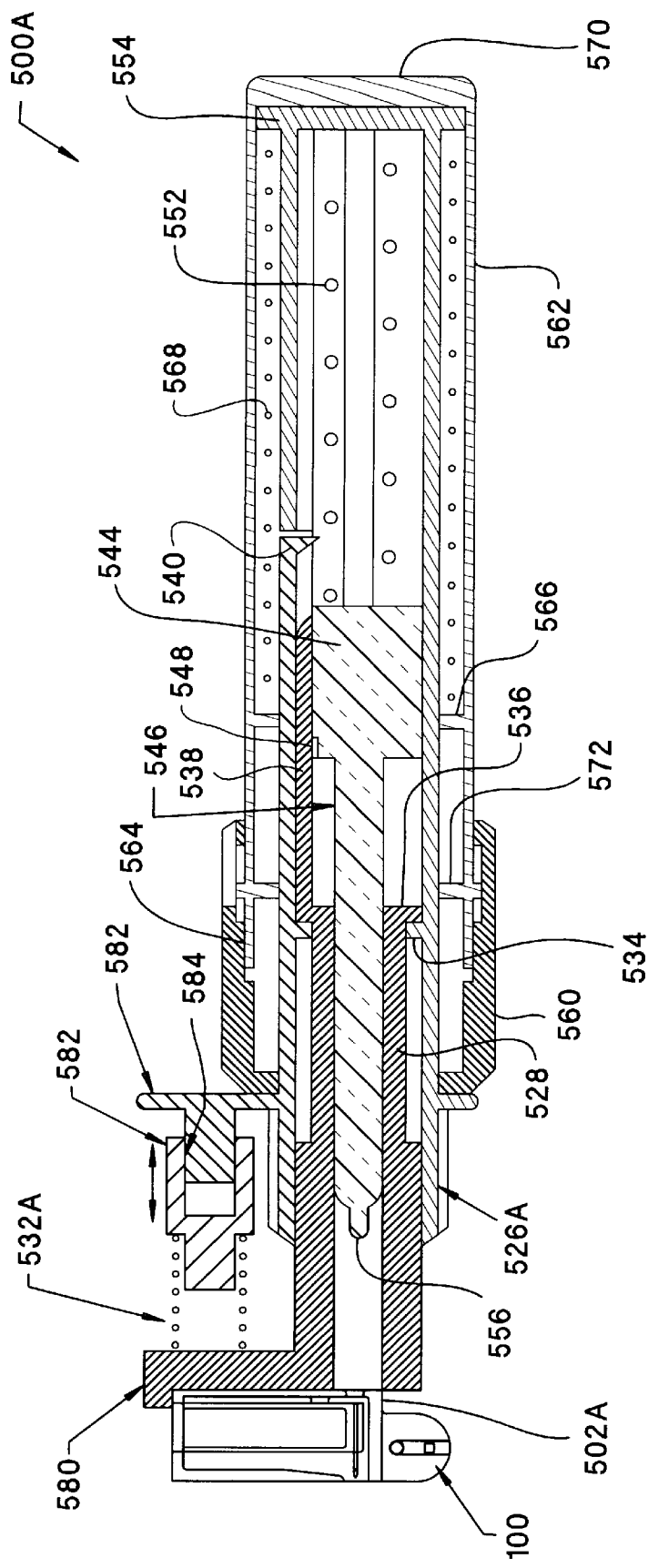
FIG. 5 shows a sectional view in portion of an embodiment of a blood sampling device with a flat test cartridge.

The driver for driving the lancing device of FIGS. 4A–4C can also be adapted to be used for driving the flat test cartridge in a lancing device. FIG. 5 shows such a lancing device that can provide reproducible lancing. Generally, this lancing device 500A has features similar to those of FIGS. 4A and 4B, including, a casing 526A, force adjuster 528, flange 534, preload adjuster spring 532A, adjuster flange 536, trigger 538, catch 540, plunger 542 having a larger base 544 and a long, more slender shaft 546, small recession 548, protruding tabs 550 not shown in the FIG. 5, driving spring 552, casing base 554, tip 556, depth adjuster 560, cocking tube 562, tube spring 568, and tube base (or closed end) 570. However, because of the difference in shape between the flat and the bar-shaped test cartridges, in FIG. 5, the cartridge holder 502A can have guard ridges (not shown) on a mount 580 that restrains the test cartridge 100 so that the test cartridge can be slid into position and that the cartridge case will not be moved distally when the plunger 542 pushes the lancet distally. The casing 526 has an elbow 582 with threads 584 matched to a preload adjuster 586 for adjusting the preload force resulting from the preload adjuster spring 532A compressing on the mount 580. Details of a few embodiments of lancing devices suitable for using test cartridges for lancing is disclosed in the copending U.S. patent application Docket Ser. No 10971582-1, entitled "Reproducible Lancing for Sampling Blood" filed on the same day and commonly assigned to the same assignee as the present application, said copending application is incorporated by reference in its entirely herein.

In the embodiment shown in FIGS. 1A and 1B, the test cartridge has a generally thin and flat shape. The thin, flat design of the cartridges permits several cartridges to be packaged (in a stack) in a small cassette, similar in design to existing dispensers of single-edged razor blades. Briefly described, such a cassette 150 (shown in FIG. 7) includes a compartment 152 that contains a plurality of new, unused test cartridges 100, typically pressed to one side of the cassette 150 at an exit port 156 of the cassette by a spring 160A, in a manner similar to cassette of common two edged razor blades. In addition, there can be a compartment for storing used test cartridges 158, which can also be held against the cassette wall by a spring. Furthermore, cassettes holding bar-shaped test cartridges can also be made. When needed, a cartridge can be slid off the cassette and be deployed in the appropriate lancing device. Such cassettes can be incorporated into the glucometers disclosed in this application. Details of a few embodiments of cassettes for holding flat test cartridges and for holding bar-shaped test cartridges are disclosed in copending application Docket Ser. No. 10970749-1 (supra).

Glucometer

Figure 6:
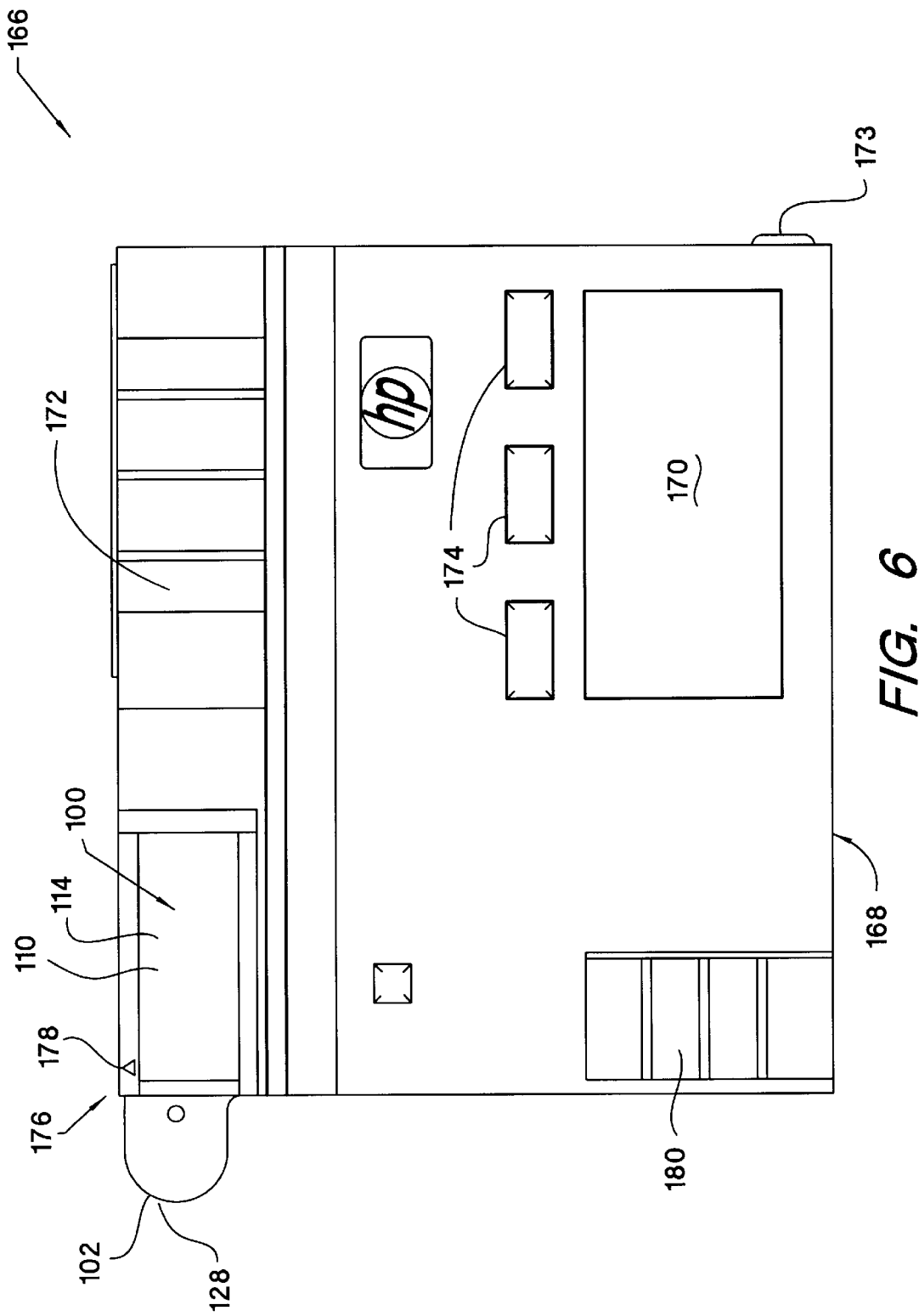
FIG. 6 shows a plan top view of a glucometer deploying a flat test cartridge.

FIG. 6 shows a plan view of a glucometer in which a flat cartridge of FIG. 1 has been installed (or deployed) and can be used for lancing. In this embodiment, the glucometer 166 has a body 168. A sweeper 172 in the glucometer can be used to sweep or push a single new test cartridge to deploy (or load) in a position for use. After use, the sweeper 172 can be used to push the used test cartridge out of the glucometer for disposal. Alternately, cartridges may also be loaded or removed individually by finger.

As shown in FIG. 6, the test portion 102 (with the sample port 128 being most remote from the body 168) sticks out from the body. Additionally, preferably, the test cartridge 100 is loaded in the body of the glucometer 166 such that the test cartridge 100 has an exposed top surface 114 with an absorbent area 110 for wiping excess blood from the finger if necessary at the end of sampling and analyzing blood. Furthermore, a mark 178 can be molded or printed into the glucometer to show the location of the lancet hole 176 (corresponding to the location of the finger for lancing) through which the lancet will protrude to lance the skin of a patient.

Figure 7:
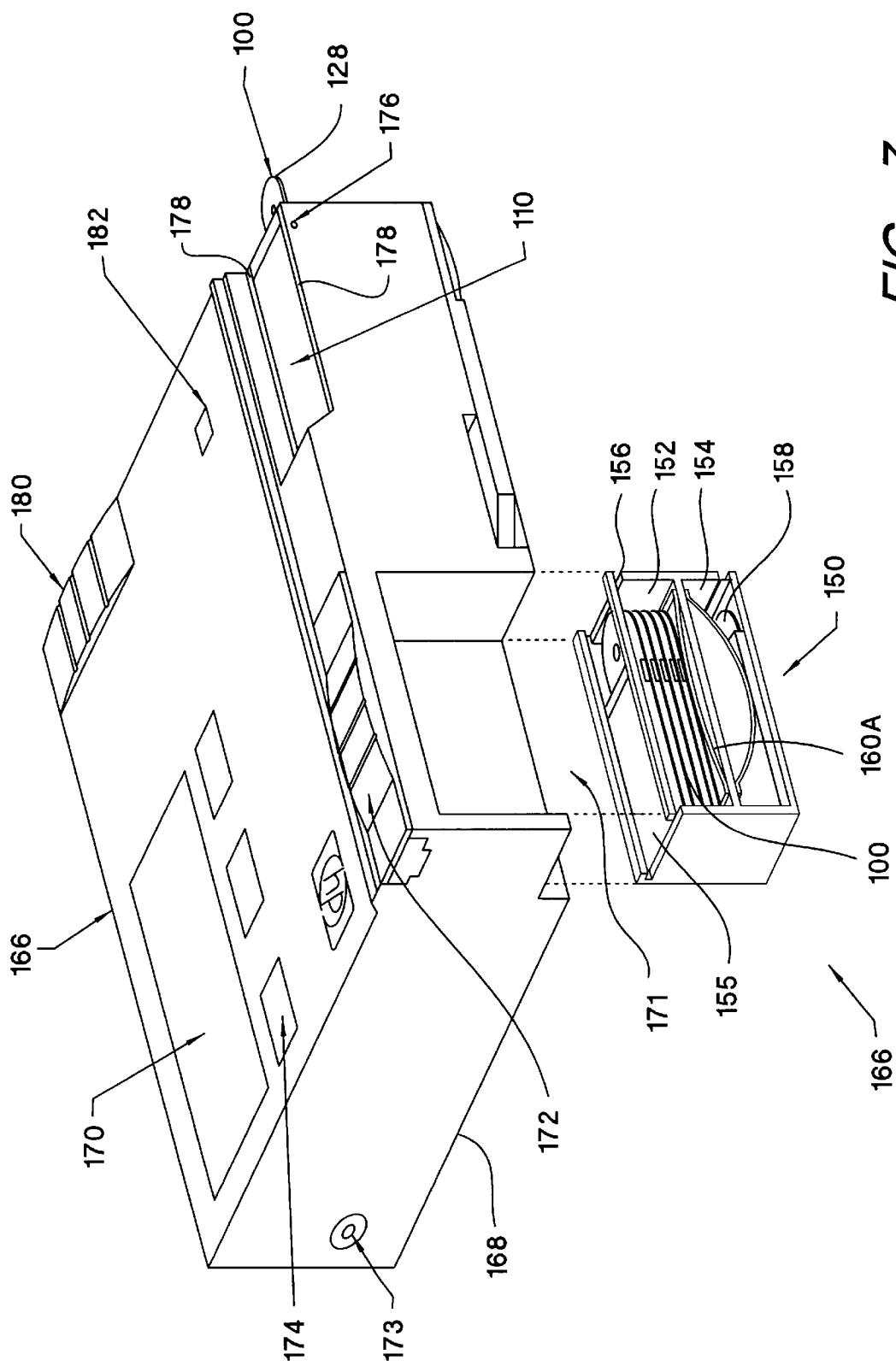
FIG. 7 shows an isometric view of an embodiment of an embodiment of the glucometer of the present invention for use with a cassette of flat test cartridges.

In the embodiment shown in FIG. 7, the glucometer 166 has a body 168 that has a recess 171 for receiving and securing the cassette 150. The recess 171 is adjacent to a sweeper 172 to sweep single cartridges to deploy (or load) in a position for use. The sweeper 172 can have a pusher finger that reaches to the end of the top test cartridge 155 in the cassette remote to the exit port 156 and, with a sweeping motion, can push the top test cartridge to slide from the stack of new test cartridges out the exit port 156. The sweeper 172 can load single cartridges from the cassette into a position for measurement of blood parameters (or characteristics). Alternately, test cartridges may also be loaded individually without a cassette. In FIG. 7, a sweeper with sliding mechanism similar to a dispenser of single-edged razor blades, can sweep a test cartridge slidingly over another test cartridge into the deploy position (with the test portion 102 of a test cartridge protruding from body of the glucometer). The same mechanism can eject the test cartridge after use for proper disposal.

The body 168 further has electronic circuits including a processor (which is not shown) to control and read the results of an analysis using the test cartridge. (A more detailed description of the instrument will follow). Analysis data and other information, e.g., date and time, can be displayed in a display (e.g., LED or LCD display). The display can show the measured blood glucose concentration (e.g., in a large font for visually impaired users) and any information about the status of the measurement. On the body 168, electrical data port 173 enables electrical communication of data between the body 168 and external electronics, such as a remote computer, display unit, data storage, and the like. This data port 173 allows the transfer of data out of (or into or both) the glucometer 166, e.g., past glucose readings stored in memory. The port may also load data, programs, or information from a physician's computer. Further, electronic connections can be present in the glucometer 166 to connect electrically the processor to electrical contacts in the test cartridge to permit electrical communication, including data and instruction transmission, between the test cartridge, and the processor. Alternatively, data communication between the glucometer and a heathcare provider can be by way of wireless transmission. Control buttons 174 on the body 168 permit programming and set-up of the instrument (setting date, time, language preference, scrolling through stored values, on/off settings, instrument diagnostics, etc., as well as sending or receiving information to electronics external to the body).

To allow easy access to the lanced skin, the sample port 128 of the loaded test cartridge can be positioned at a more pointed area (or an area with more curvature) of the test cartridge. As shown in FIG. 6, the test portion 102 (with the sample port 128 being most remote from the body 168) sticks out from the body. Additionally, preferably, a test cartridge is loaded in the body of the glucometer such that the test cartridge has an exposed top surface (see FIG. 6). The exposed top of the test cartridge has an absorbent area for wiping excess blood from the finger if necessary at the end of a test. Furthermore, a mark 178 can be molded or printed into the glucometer to show the location of the lancet hole 176 (corresponding to the location of the finger for lancing) through which the lancet will protrude to lance the skin of a patient.

FIG. 7 shows a test cartridge 100 in place for use, with the sample port 128 of the cartridge protruding from the glucometer. In another configuration (see the test cartridge of FIG. 2). The lancet of FIG. 2 can protrude immediately below the lancet hole in the glucometer, so that the location of the lanced finger and the sample port are nearly coincident, thereby simplifying the transfer of blood from the wound to the test strip (and permitting potentially an automated or semi-automatic transfer of blood sample without action by the patient).

To provide a driving (or actuating) force to push the lancet for lancing, a cockable actuator 180, e.g., one that contains a sliding lever for cocking a spring-activated puncher (the spring and the puncher are not shown) to hold the spring in a compressed state until released, can be used. For a glucometer that contains a driver of FIG. 5, after cocking the spring in preparation for lancing, the test cartridge can be pressed against the skin site (which is to be lanced) to release the spring-activated puncher to drive the pre-loaded lancet. As a result, the lancet tip is driven to extend out of the test cartridge 100. Alternatively, a separate button (e.g., button 182) can be used, when pressed, to release the spring-activated puncher. A driver different from those disclosed in FIGS. 4 and 5, releasable by buttons or otherwise, is contemplated, since some cocking mechanisms for spring-activated drivers are known in the art. The lancing button 182 preferably is located away from the control buttons 174 and has a different color and markings for preventing from being activated inadvertently. For example, the lancing button 182 can be located in a recess or inside a protective frame.

For the embodiment of flat test cartridges shown in FIG. 2, a glucometer similar to that shown in FIG. 6 can be used. Generally, that glucometer would have the same features as that of FIG. 6. When a flat test cartridge of FIGS. 1A and 2B is installed in the glucometer, the glucometer with the test cartridge would look like that of FIG. 6 except for the absence of the test portion 102 shown in FIG. 6. In the case of the test cartridge of FIG. 2, the test area 124C for receiving and analyzing blood is at the lancet exit port 133C.

Figure 8A:
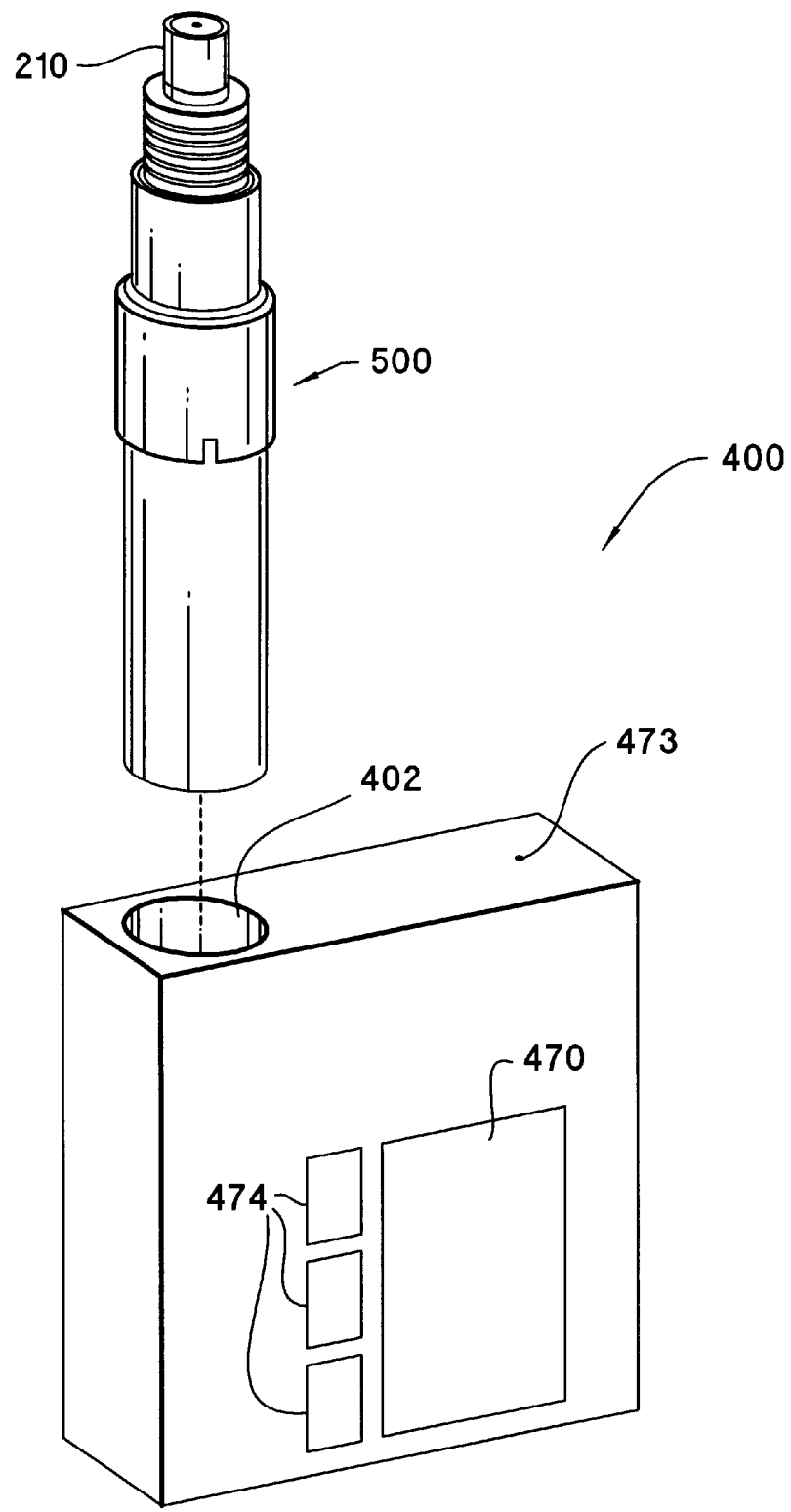
FIG. 8A shows an isometric view exploded in part, of a glucometer for a bar-shaped test cartridge.
Figure 8B:
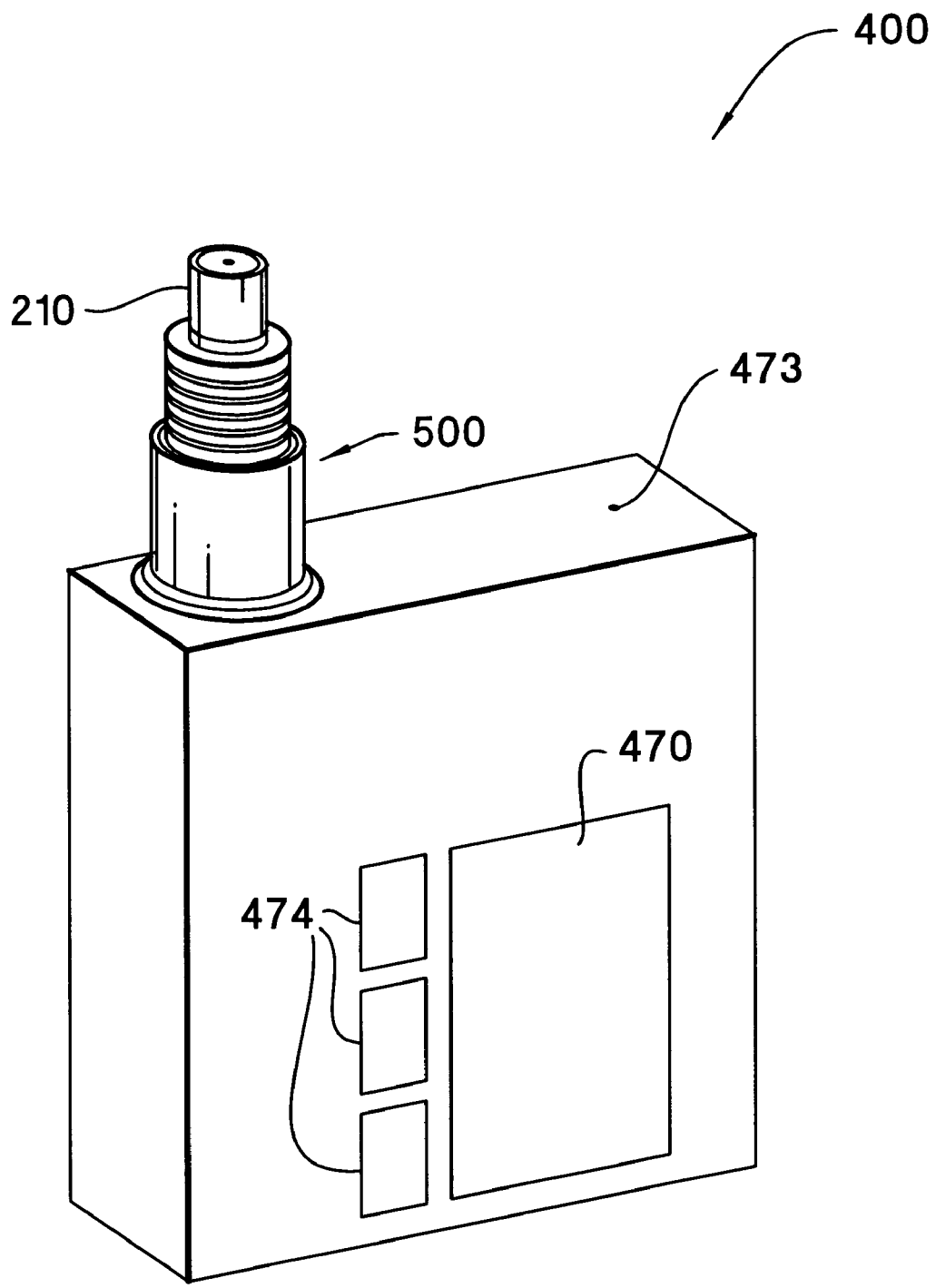
FIG. 8B shows an isometric view of the glucometer of FIG. 8A.

A glucometer for use with a bar-shaped test cartridge can have driving mechanisms, data processing electronics, as well as display and control systems similar to those for the flat type test cartridges. An embodiment of a glucometer suitable for use with the bar-shaped test cartridge shown in FIGS. 3A–3D is shown in FIG. 8A and FIG. 8B. As previously stated, an embodiment for the driving mechanism that enables reproducible lancing for such test cartridges is shown in FIGS. 4A and 4B. FIG. 8A is a partially exploded view and FIG. 8B is an isometric view showing a glucometer 400 having a lancing device 500 like that described above. The lancing device 500 is inserted into a receptacle slot 402 which can hold the lancing device tightly, for example, by threads or interlocking pins and notches, clips, screws, and the like. Electrical contacts in the body of the glucometer 400 and the lancing device 500 provide electrical communication such that information can be transferred between them. The glucometer 400, similar to the glucometer in FIG. 6, can have control buttons 474, display 470, as well as data port 473 for communication with an external device such as a computer or a doctor's remote monitoring system.

Glucometers With More Ergonomic Features

Figure 9:
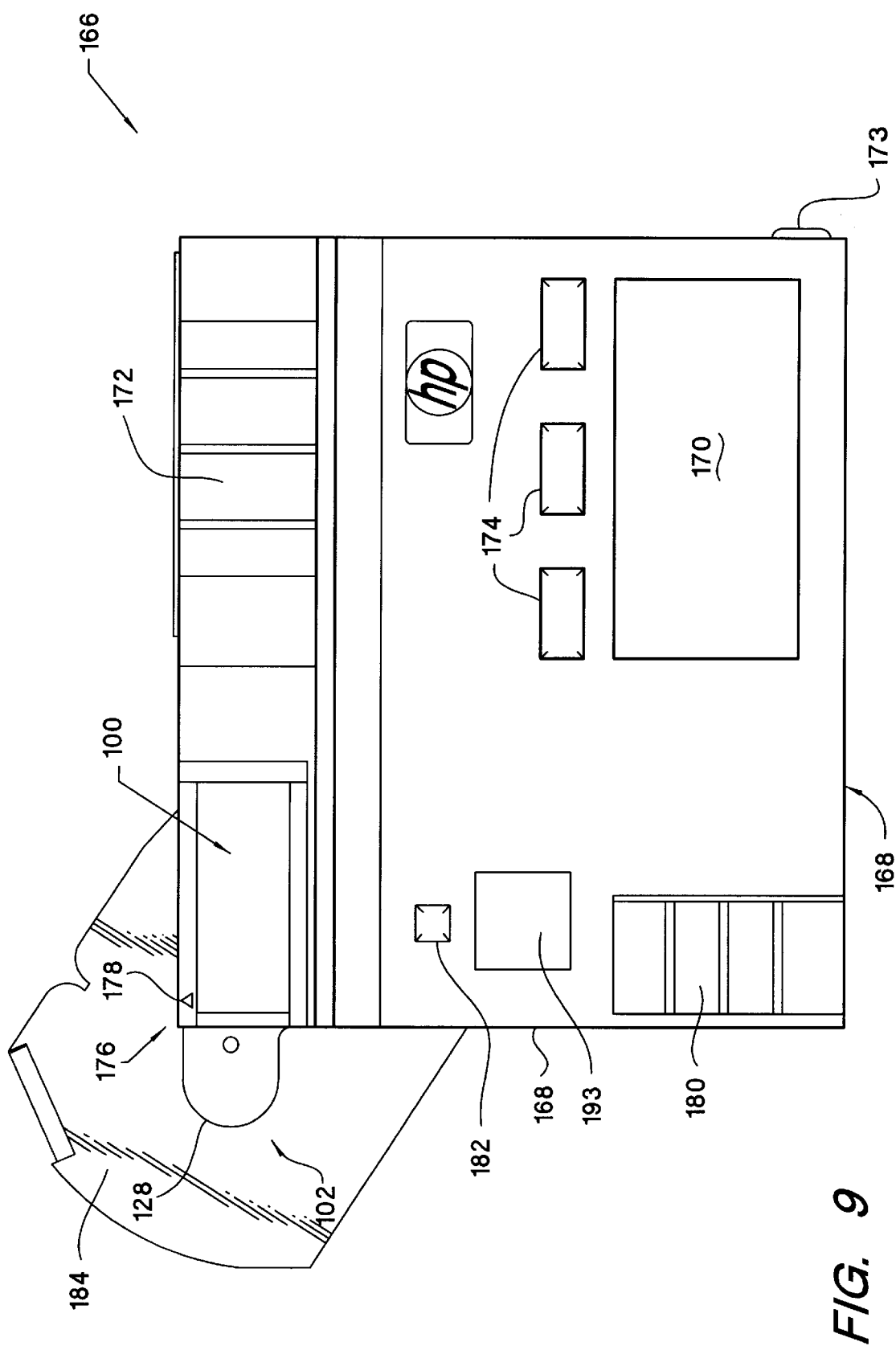
FIG. 9 shows a plan top view of a glucometer similar to FIG. 7, having a finger rest.
Figure 10:
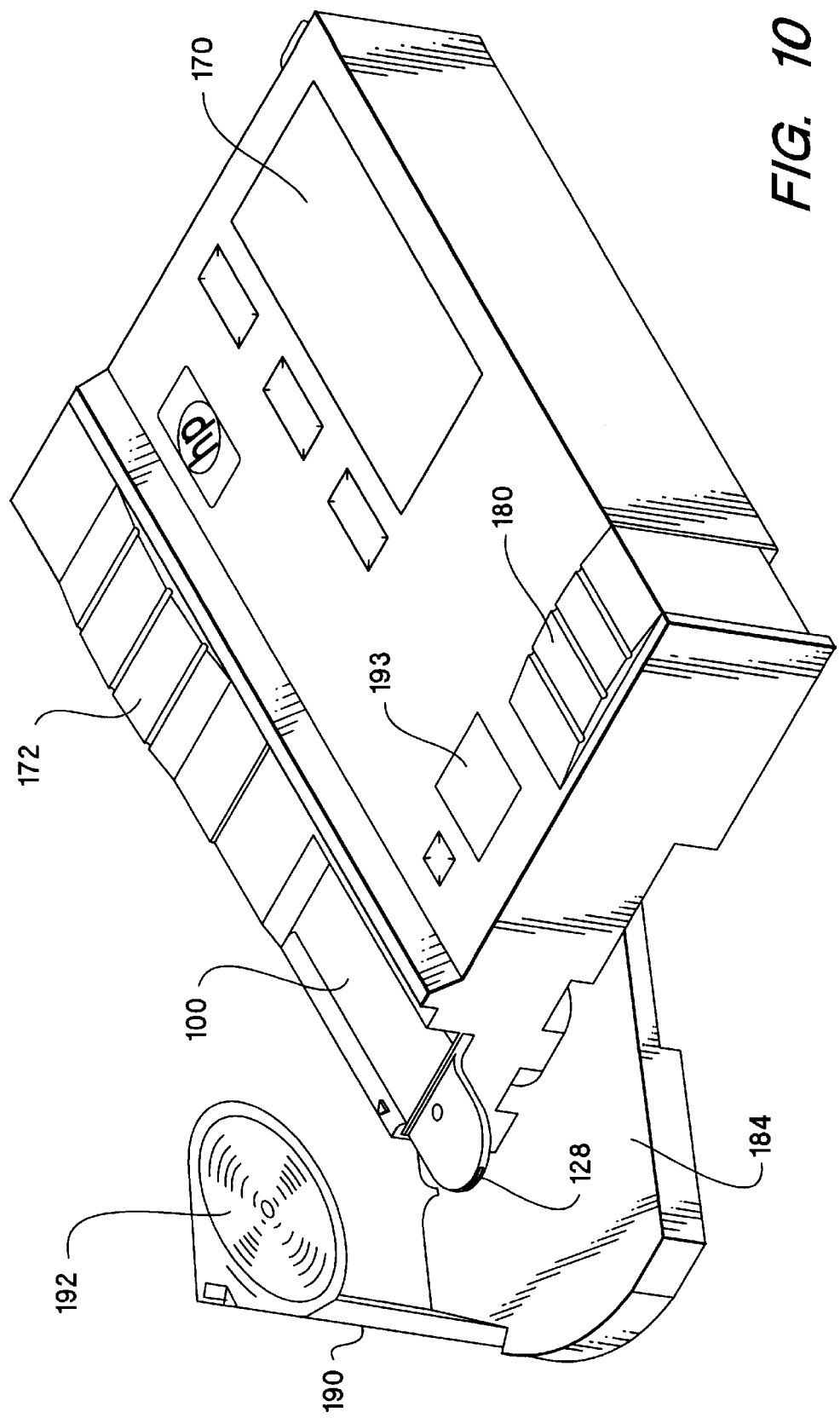
FIG. 10 shows an isometric view of the glucometer of FIG. 9, showing a lens.
Figure 11:
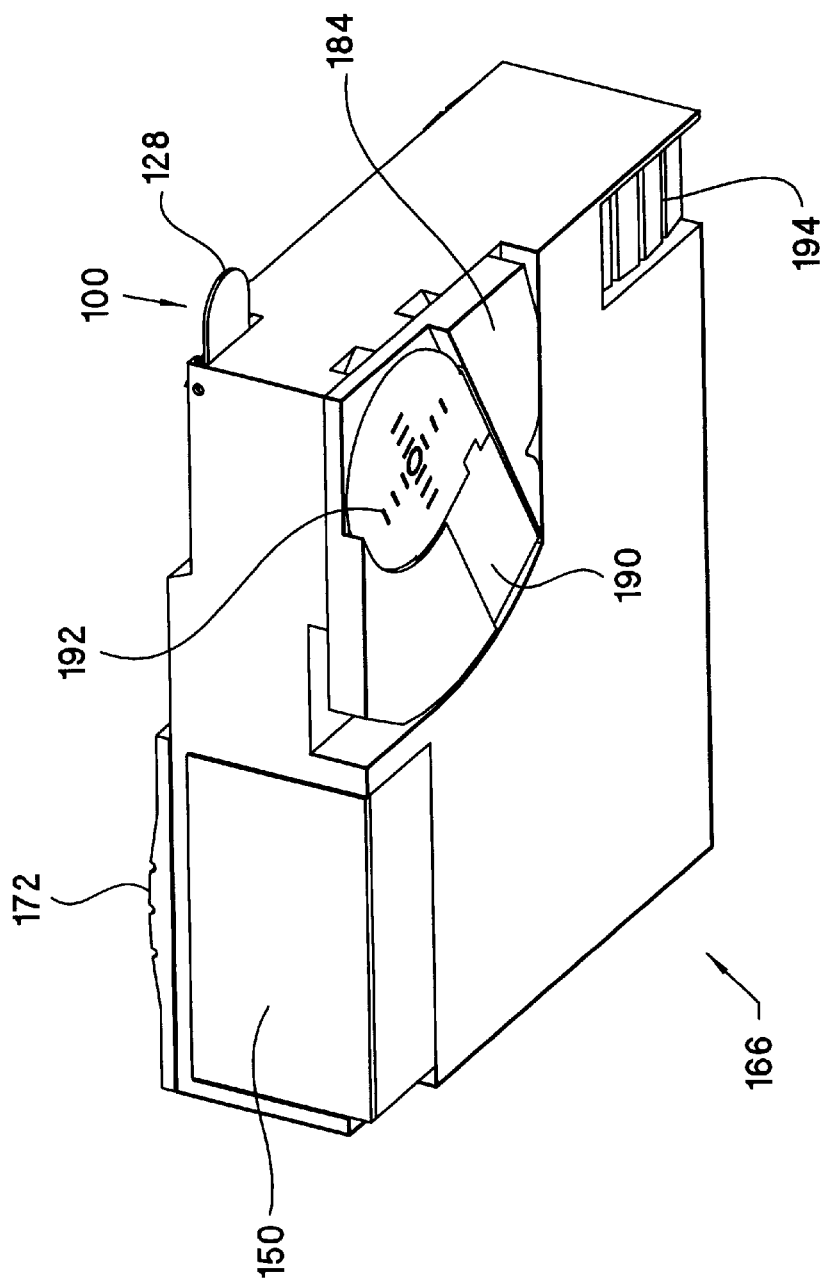
FIG. 11 shows another isometric view from another perspective of the glucometer of FIG. 10.

A glucometer of the present invention can have various features that improve the ergonomic functionality. FIG. 7 is an isometric view showing an embodiment of how a cassette 150 containing test cartridges similar to those described above can be attached to an instrument (glucometer) that can process and display data showing properties of blood sampled with the test cartridges. The cassette 150 has a compartment 152 for containing new cartridges and another compartment 154 for containing used (i.e., spent) cartridges. FIG. 9 shows a plan view of a glucometer, similar to the one of FIG. 6, further showing a finger shelf 184, which allows a person to steady a finger against the glucometer for lancing the finger and sampling blood from the lanced finger. Preferably, to achieve a compact arrangement with less bulk, the finger shelf fits under the instrument when not in use. FIG. 10 shows the finger shelf 184 in the glucometer 166 being unfolded and rotated out from a corner location, whereas FIG. 11 shows the glucometer when the finger shelf 184 is folded for storage. A person can position the finger to rest against the finger shelf 184 to (1) steady the finger for lancing and (2) place the blood droplet at the sample port 128 of the test cartridge 100. A detente lock (not shown) can be used to hold the shelf tight in the instrument when not in use, and holds the shelf in place during measurements.

FIG. 10 shows a projected isometric view of the glucometer 166, with the finger shelf 184 extended for use. In addition, a lens 188 is shown at the end of an arm 190 attached to the finger shelf 184. The lens 188 and arm 190 can preferably fit flush into the finger shelf 184 for storage. A patient may optionally use the lens to (a) obtain a magnified view of the finger after lancing, (b) judge the size of the droplet of blood, and (c) assist the patient in placing the droplet on the small sample port of the test cartridge 100. The lens 188 can also have a graticule 192 molded into the material of the lens (see FIGS. 10–12), so that the patient can observe and estimate (under magnification) the size of the blood droplet on the finger and observe the sample port 128 on the test cartridge 100. The graticule 192 has markings which gauge the proper size droplet that suits the test cartridge 100 for a successful measurement. Thus, the patient may judge more easily how much blood to "milk" from the finger. Using exactly the right amount of blood that suits the test cartridge has additional benefits, such as (1) permitting a minimally sized wound from the lancet (and concomitant minimal pain), and (2) eliminating excess blood on the finger which may soil clothes and equipment. The patient may wipe any excess blood on the absorbent top covering 110 of the test cartridge, eliminating the need to carry extra tissues or bandages. The absorbed blood thus remains with the test cartridge for proper disposal, further reducing the risk of transmitting blood borne diseases. Further, chemical agents can be included in the absorbent top covering 100 for cleaning or antiseptic purposes.

The embodiment shown in FIG. 10 also includes a heating pad 193 on the top surface of the glucometer 166. This heating pad can have electrically heated elements (not shown) that can be activated by the control buttons 174 or some other switches. The heating elements can be covered with a cover made of heat retaining materials such as cloth, plastic, woven synthetic fibers etc. to distribute and retain heat and prevent burning the user. The heating elements can be heated by electricity from the line, or alternatively, by battery. The heating pad 193 can also be positioned on other convenient surfaces of the glucometer.

For further clarity, FIG. 11 shows the underside of the glucometer 166 with the cassette 150 attached and the finger shelf 184 folded into the glucometer body 168 for storage. The arm 190 and the lens 188 with graticule 192 are shown folded into the finger shelf 184 for storage. The bottom of the test cartridge 100 is visible, protruding from the upper portion of the glucometer 166. The cockable actuator 180 for driving the lancet is also visible at the bottom of the glucometer 166. Although any movable cocking arrangement can be used, preferably, the cocking actuator has a piece 194 that wraps around to extend from the top side to the bottom side of the glucometer 166, so that the piece 194 may be grasped by two fingers and pulled out to cock the lancing spring. Preferably, the surface of the cocking piece 194 is below the surface of the glucometer to prevent indiscriminate contact or inadvertent cocking.

Figure 12:
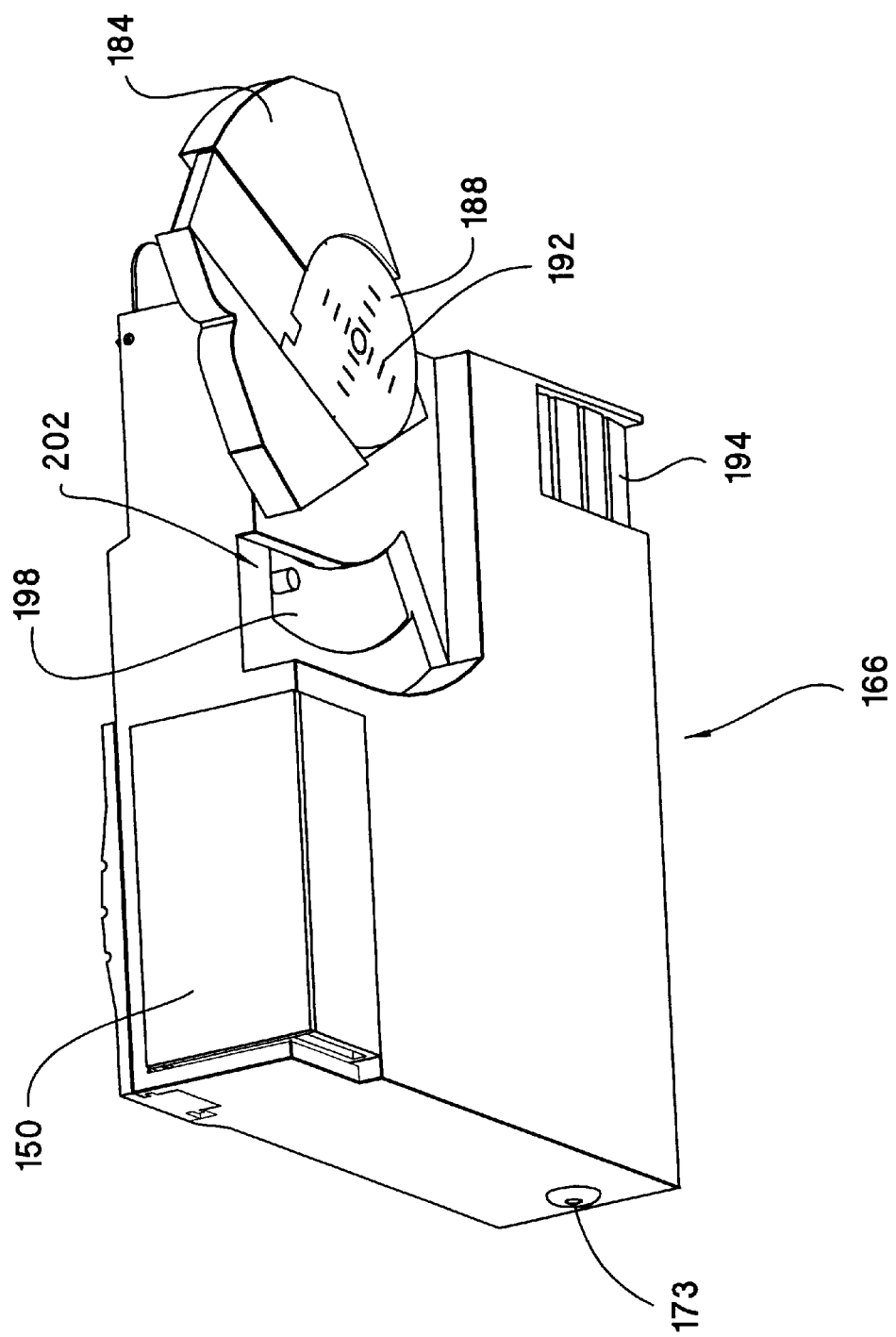
FIG. 12 shows another isometric view of the glucometer of FIG. 11, showing further details.

Since all fingers do not have the same size or vascular structures, they may require different depth of penetration by a lancet to yield a specific amount of blood. FIG. 12 illustrates an embodiment in which the glucometer 100 has an adjustable mechanism to adjust the extent of lancet protrusion from the glucometer. FIG. 12 shows the underside of the glucometer 166 with the finger shelf 184 rotated out for use (but with the arm 190 and lens 188 still folded into the finger shelf). The rotation of the finger shelf 184 reveals a cavity 202 in the underside of the glucometer 166 approximately the size of a finger. The cavity 202 contains a sliding switch 198 that provides an adjustment for the lancet. Sliding the switch 198 moves an internal part which controls the maximum excursion of the lancet (and therefore the depth of the lancet wound). The patient can move the switch 198 to an optimal location where the lancet causes minimal pain while permitting an adequate blood sample. The switch 198 can be held in place by friction, and the recessed location under the finger shelf 184 prevents undesired adjustments. A patient can set a depth for the lancet once and need not attend to it further. However, if desired, new adjustments are easy to make by a small motion of the switch.

Figure 13:
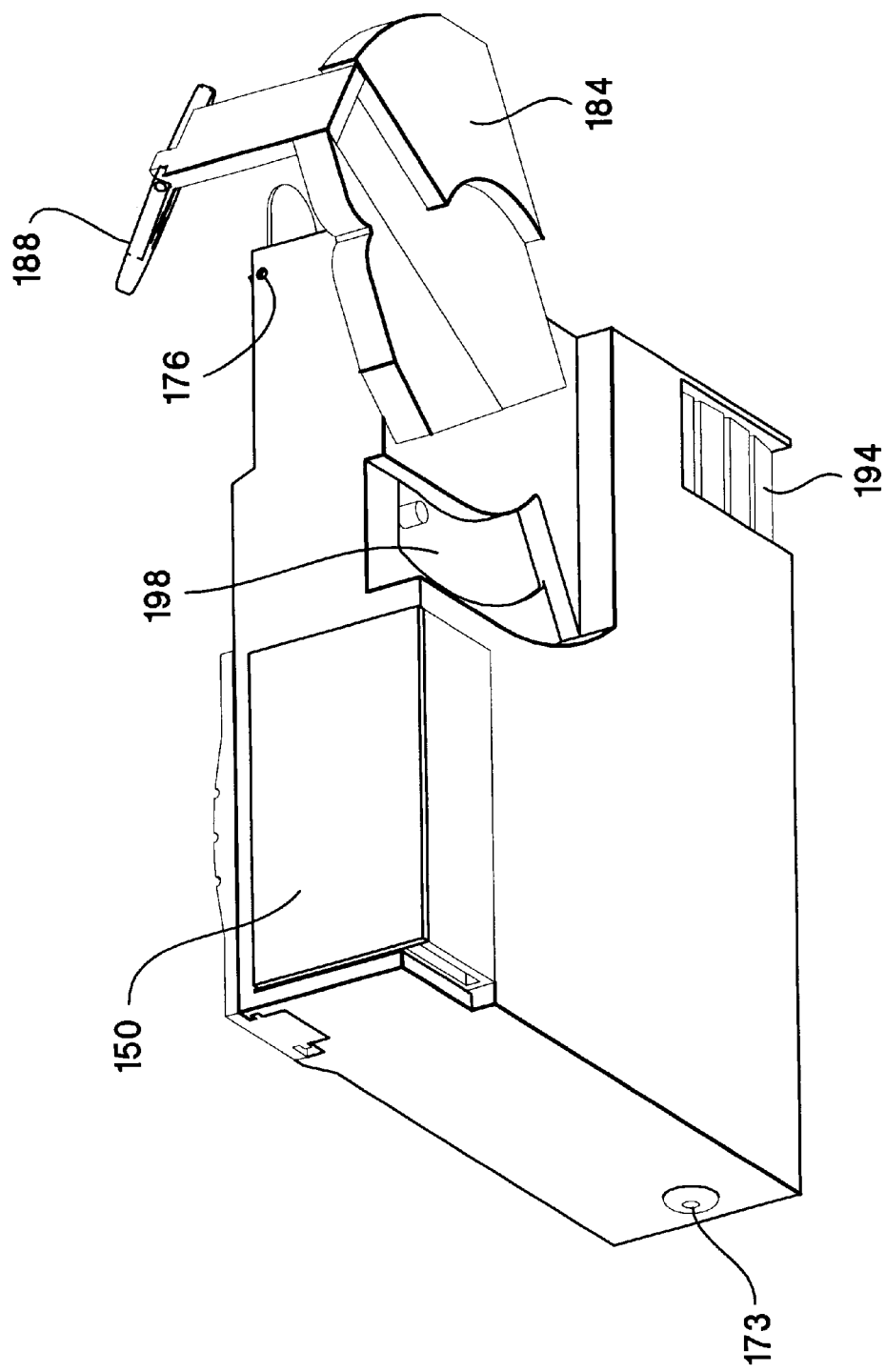
FIG. 13 shows another isometric view of the glucometer of FIG. 11, showing a finger shelf and arm connected to a lens and graticule.

For further clarity, FIG. 13 shows the same view as FIG. 12, except that the arm 190 and lens 188 are extended for use, revealing the features that allow these pieces to fold into the finger shelf 184.

For conventional glucometers (e.g. GLUCOMETER ELITE glucose meter, Miles Inc. Elkhart, Ind., and ONE TOUCH PROFILE glucose meter, Lifescan, Milpitas, Calif.), check strips that electronically tests the glucometer and test strips that electronically informs the glucometer about the quality or characteristics of the batch of the test strips are being used. In some systems, the batch of test strips is coded and the glucometer is adjusted (i.e., calibrated) according to the code of the particular batch. Such testing and coding techniques are known in the art. To ensure that the glucometer functions properly and to adjust for the variation of the quality of test cartridges, check cartridges and coding mechanisms based on the electronics and chemistry of such convention testing and calibrating techniques can be used to check and adjust the function of the glucometer before a person uses the instrument and test cartridges for sampling and analyzing blood.

To illustrate the use of the embodiments of the glucometers, for example, e.g., that of FIG. 12, a test cartridge 100 is loaded (or deployed) in the glucometer and the spring-actuated driver is cocked to get the glucometer ready to lance a finger. When the cocked driver is released, the driver pushes the lancet to lance the finger. One uses sensation of touch and pressure in order to pre-load the lancet device against the skin in a reproducible manner. The right "touch" varies with each individual, but is relatively constant for a given individual, and is a function of the lancing device and skin characteristics. As mentioned earlier, lateral edges of the fingers are the preferred location. In an embodiment in which a test cartridge has a small lancet, e.g., one similar to the ULTRA-FINE lancet, there often is no spontaneous bleeding from the wound. Further, some users may find a "sweet spot," where pain from lancing is minimal. After a lancet has pierced the lateral edge of a finger successfully, a convenient way to educe blood from the wound site is to press gently on the fingertip near the wound where the tissue is soft. A gentle push for a second will promote a few microliters of blood to appear as a stationary droplet (to get a droplet of a 2–20 $\mu l$, which is a sufficient sample for glucose measurements). With a small wound, the lack of spontaneous bleeding after testing is also convenient to the patient because no messy, leaking wound remains, which can soil objects or can require protection. Also, the residual scarring is minimal, which is helpful if the patient must return to the same site later for additional samples—a problem with patients who make frequent tests.

The droplet of blood can be exposed to sample port 128 and transferred to the test area 124 to be analyzed. Result of the analysis is transferred electrically through electrical contacts, wires, and connections to the processor. The control buttons 174 can be used to control the analysis of the blood sample, as well as transferred information and data to external devices, e.g., computers, data storage, display, etc., through the data port 173. After analysis and data collection, the used test cartridge can be ejected and stored in the chamber 154 for spent cartridges in the cassette 150.

The ergonomic features described hereinabove for the a glucometer using the flat test cartridges can be incorporated into a glucometer for the bar-shaped test cartridges.

Although the preferred embodiment of the present invention has been described and illustrated in detail, it is to be understood that a person skilled in the art can make modifications within the scope of the invention. For example, it is contemplated that the body of a lancing device of FIG. 4 can include electronics and displays for analyzing, organizing, and displaying the information generated by the test area in the test cartridge.

What is claimed is:

1. A blood sampling apparatus for sampling blood from the skin of a patient for analysis, comprising:
   (a) a cartridge having
      (i) a cartridge case;
      (ii) a lancet housed in the cartridge case and operatively connected thereto such that it is drivable to extend outside the cartridge case through a lancing opening for lancing the skin to yield blood;
      (iii) associated with the cartridge case a compartment for receiving blood;
   (b) a housing having a driver for associating with the lancet to urge the lancet to extend outside the cartridge case, the cartridge being detachably held in said housing such that the cartridge can be disassociated from the driver after sampling blood; and
   (c) means for analyzing blood connected with the compartment in the cartridge for blood to flow therefrom to said means for analyzing blood without moving the position of the cartridge in the housing after lancing.

2. The apparatus according to claim 1 further comprising a cassette including a cartridge compartment for detachably housing one or more new cartridges, the cassette being detachably connected to the housing.

3. The apparatus according to claim 2 wherein the housing includes a means for transferring a new cartridge from the cassette to a lancing position without the patient touching the new cartridge.

4. The apparatus according to claim 2 further comprising a second cartridge compartment for receiving one or more spent cartridges.

5. The apparatus according to claim 2 further comprising a calibration cartridge.

6. The apparatus according to claim 2 wherein the cartridge case includes an identification feature visible while the cartridge is in the cassette.

7. The apparatus according to claim 1 wherein the cartridge further comprises a port near to the lancet for receiving blood from the skin after lancing and a channel in communication with the compartment for receiving blood.

8. The apparatus according to claim 1 wherein the cartridge further has a compartment for containing blood, said compartment being visible to the user to observe blood entering therein.

9. The apparatus according to claim 1 further comprising a compressor associated with the housing for processing of data after analyzing the blood.

10. The apparatus according to claim 9 further comprising a display associated with the housing for displaying analysis information.

11. The apparatus according to claim 7 further comprising a finger rest near the port external to the cartridge.

12. The apparatus according to claim 1 further comprising a heating pad for warming a site to be lanced.

13. The apparatus according to claim 1 further comprising a magnifying lens movably and operatively connected to the housing for viewing the skin during blood sampling.

14. The apparatus according to claim 13 wherein the lens has graticule thereon.

15. The apparatus according to claim 1 wherein the lancet has a tip for piercing and the apparatus further comprises a port associated with the compartment for receiving blood and within about 25 mm of the tip of the lancet when the lancet is extended for receiving blood from the skin after lancing, such that less than about 25 mm of movement of the lanced skin relative to the port is needed to expose the port to the lanced skin after lancing.

16. The apparatus according to claim 15 wherein the port is in communication with the compartment via a channel which is capable of drawing blood into the compartment by capillary force.

17. The apparatus according to claim 1 wherein the cartridge includes two surfaces on opposite sides to facilitate stacking cartridges together such that one cartridge can be slid off a stack of cartridges while the other cartridges in the stack are retained.

18. The apparatus according to claim 1 wherein the cartridge further comprises an absorbent surface associated with the cartridge case for wiping blood off the skin.

19. The apparatus according to claim 1 wherein the driver has a spring providing a preload force on the skin which is to be lanced when the skin is pressed against the cartridge, such that the skin pressing harder than a preset value of the preload force will actuate the driver to drive the lancet distally at the skin.

20. The apparatus according to claim 1 wherein the driver has screwthread matching parts adjustable to vary the distance a tip of the lancet is driven outside the cartridge case.

21. The apparatus according to claim 1 further comprising:
   a magnifying lens movably and operatively connected to the housing for viewing the skin during blood sampling;
   a port associated with the compartment for receiving blood and within about 25 mm of a sharp tip of the lancet when the lancet is extended for receiving blood from the skin after lancing, such that less than about 25 mm of movement of the lanced skin relative to the port is needed to expose the port to the lanced skin after lancing;
   a finger rest associated with the housing near the port; and
   a cassette detachably connected in the housing, the cassette including a first compartment for detachably housing one or more new cartridges and a second compartment for receiving one or more spent cartridges, the cassette having an opening for dispensing a new cartridge from the cassette to operatively connect with the driver for lancing motion.

22. A method for sampling blood from the skin of a patient, comprising:
   (a) providing a lancing apparatus having a detachable cartridge and an analytical region, the cartridge having a lancet with a lancet tip shielded in the cartridge;
   (b) driving the lancet to extend the lancet tip out of a cartridge such that the lancet pierces the skin to yield blood;
   (c) transferring blood yielded from the skin into the cartridge; and
   (d) upon the blood entering the cartridge transferring blood to the analytical region without moving the position of the cartridge in the apparatus.

23. The method according to claim 22 further comprising deploying the cartridge in a support of the lancing apparatus before driving the lancet to lance.

24. The method according to claim 23 further comprising holding a cassette for storing new cartridges in the support to prepare for transferring a new cartridge from the cassette to be deployed in the support for lancing the skin.

25. The method according to claim 22 further comprising, after driving the lancet to pierce the skin, exposing a site of the cartridge to blood resulting from lancing the skin to analyze the blood.

26. The method according to claim 22 further comprising, after transferring blood into the cartridge, processing data of blood analysis by an electronic processor and displaying the result of analysis.

27. The method according to claim 22 further comprising, in transferring blood into the cartridge, exposing a port on the cartridge to blood resulting from lancing the skin, the port being in fluid communication to an analytical compartment for analysis of blood.

28. The method according to claim 27 wherein the port is within about 25 mm from the tip of the lancet after extension thereof for lancing such that less than about 25 mm of movement of the skin relative to the port is needed to expose the port to blood from the skin after lancing.

29. The method according to claim 22 further comprising positioning a magnifying lens adjustably connected to a support housing of the lancing apparatus for viewing the skin for lancing.

30. The method according to claim 23 further comprising, in driving the lancet, pressing the cartridge against the skin to be lanced to trigger the lancing apparatus to drive the lancet towards the skin.

31. The method according to claim 22 further comprising adjusting the extent the lancet tip can be driven out of the cartridge case before driving the lancet.

32. The method according to claim 23 further comprising flowing the blood into the analytical region for analysis after lancing the skin, said analytical region being inside the cartridge.

* * * * *